(12) United States Patent
Schwink et al.

(10) Patent No.: US 7,319,108 B2
(45) Date of Patent: Jan. 15, 2008

(54) ARYL-SUBSTITUTED HETEROCYCLES, PROCESS FOR THEIR PREPARATION AND THEIR USE AS MEDICAMENTS

(75) Inventors: Lothar Schwink, Stadtallendorf (DE); Siegfried Stengelin, Eppstein (DE); Thomas Boehme, Ruesselsheim (DE); Matthias Gossel, Hofheim (DE); Gerhard Hessler, Hofheim (DE); Petra Stahl, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 277 days.

(21) Appl. No.: 11/042,563

(22) Filed: Jan. 25, 2005

(65) Prior Publication Data
US 2005/0176710 A1   Aug. 11, 2005

Related U.S. Application Data

(60) Provisional application No. 60/584,458, filed on Jun. 30, 2004.

(30) Foreign Application Priority Data
Jan. 25, 2004   (DE) .................. 10 2004 003 812

(51) Int. Cl.
  *A61K 31/4245* (2006.01)
  *C07D 271/10* (2006.01)
(52) U.S. Cl. ..................... 514/364; 548/143
(58) Field of Classification Search ......... 514/364; 548/143, 145
See application file for complete search history.

(56) References Cited

U.S. PATENT DOCUMENTS

| 6,288,061 B1 | 9/2001 | Sueoka et al. |
| 2005/0209213 A1 | 9/2005 | Ishihara et al. |

FOREIGN PATENT DOCUMENTS

| WO | WO 97/26258 | 7/1997 |
| WO | WO 00/66578 | 11/2000 |
| WO | WO 01/21577 | 3/2001 |
| WO | WO 01/82930 | 11/2001 |
| WO | WO 02/02744 | 1/2002 |
| WO | WO 02/06245 | 1/2002 |
| WO | WO 02/10146 | 2/2002 |
| WO | WO 02/057233 | 7/2002 |
| WO | WO 02/079200 | 10/2002 |
| WO | WO 02/089729 | 11/2002 |
| WO | WO 03/045313 | 6/2003 |
| WO | WO 03/087044 | 10/2003 |
| WO | WO 03/089418 | 10/2003 |
| WO | WO 03/097047 | 11/2003 |
| WO | WO 2004/072025 | 8/2004 |
| WO | WO 2004/111045 | 12/2004 |

OTHER PUBLICATIONS

Chang et al., Bioorganic & Medicinal Chemistry Letters 11 (2001) 2549-2553.*

* cited by examiner

*Primary Examiner*—Rebecca Anderson
*Assistant Examiner*—Michael P. Barker
(74) *Attorney, Agent, or Firm*—Barbara E. Kurys

(57) ABSTRACT

The invention relates to substituted aryl-substituted heterocycles and to the physiologically tolerated salts and physiologically functional derivatives thereof, to process for their preparation and to their use as medicaments.
Compounds of the Formula I

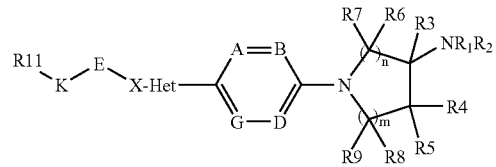

in which the radicals have the stated meanings, the N-oxides thereof, and the physiologically tolerated salts thereof, and process for the preparation thereof are described. The compounds bring about for example a weight reduction in mammals and are suitable for example for the prevention and treatment of obesity and diabetes.

12 Claims, No Drawings

ARYL-SUBSTITUTED HETEROCYCLES, PROCESS FOR THEIR PREPARATION AND THEIR USE AS MEDICAMENTS

The invention relates to aryl-substituted heterocycles and to the physiologically tolerated salts and physiologically functional derivatives thereof.

Compounds similar in their overall structure to the heterocycles described herein and having a pharmacological effect have been described in the prior art. Thus, for example, WO 03/097047 describes aryl-substituted oxadiazoles for the treatment of obesity and diabetes.

Compounds with MCH-antagonistic activity for treatment of obesity are disclosed in the prior art (examples: WO2001021577, WO2003035624, WO2002089729, WO2002006245, WO2002002744, WO2002057233, WO2003045313, WO2003097047, WO2002010146, WO2003087044).

The invention was based on the object of providing compounds which bring about a weight reduction in mammals and are suitable for the prevention and treatment of obesity and diabetes.

Surprisingly, a series of compounds which modulate the activity of MCH receptors has been found. In particular, the compounds are distinguished by MCH1R antagonism.

The invention therefore relates to compounds of the formula I,

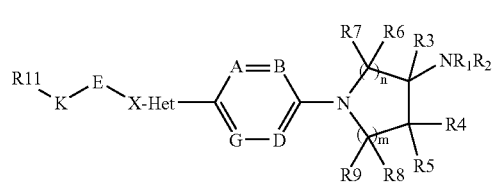

in which the meanings are

R1, R2 independently of one another H, $(C_1-C_8)$-alkyl, $-(CR13R14)_o-R12$, $(C_1-C_4)$-alkoxy-$(C_1-C_4)$-alkyl, $(C_3-C_8)$-alkenyl, $(C_3-C_8)$-alkynyl, $CO-(C_1-C_8)$-alkyl, $-CO-(CH_2)_n-R12$, $CO(C(R15)(R16))_qN(R17)(R18)$, $CO(C(R19)(R20))_sO(R21)$; or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, $CF_3$, $NO_2$, CN, $(C_1-C_6)$-alkyl, $O-(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R22), CON(R23)(R24), hydroxy, COO(R25), $N(R26)CO(C_1-C_6)$-alkyl, $N(R27)(R28)$ or $SO_2CH_3$;

o 0, 1, 2, 3, 4, 5, 6;

q, s independently of one another 0, 1, 2, 3, 4;

R15, R16, R17, R18, R19, R20, R21, R22, R23, R24, R25, R26, R27, R28 independently of one another H, $(C_1-C_6)$-alkyl;

R17 and R18, R23 and R24, R27 and R28 independently of one another optionally together with the nitrogen atom to which they are bonded a 5-6 membered ring which, apart from the nitrogen atom, may also include 0-1 further heteroatoms from the group of NH, $N-(C_1-C_6)$-alkyl, oxygen and sulfur;

R12 OH, $O-(C_1-C_6)$-alkyl, CN, COO(R29), CON(R30)(R31), N(R32)(R33), 3-12 membered mono-, bi- or spirocyclic ring which may comprise one or more heteroatoms from the group of N, O and S, and the 3-12 membered ring may comprise further substituents such as F, Cl, Br, I, OH, $CF_3$, $NO_2$, CN, $OCF_3$, oxo, $O-(C_1-C_6)$-alkyl, $(C_1-C_4)$-alkoxy-$(C_1-C_4)$-alkyl, $S-(C_1-C_6)$-alkyl, $(C_1-C_6)$-alkyl, $(C_2-C_6)$-alkenyl, $(C_3-C_8)$-cycloalkyl, $(C_2-C_6)$-alkynyl, $O-(C_0-C_8)$-alkylene-aryl, $(C_0-C_8)$-alkylene-aryl, N(R34)(R35), $CO(C_1-C_6)$-alkyl, COO(R36) and $S(O)_u(R37)$;

u 0, 1, 2;

R34, R35 independently of one another H, $(C_1-C_8)$-alkyl;

R34 and R35 optionally together with the nitrogen atom to which they are bonded a 5-6 membered ring which, apart from the nitrogen atom, may also include 0-1 further heteroatoms from the group of NH, $N-(C_1-C_6)$-alkyl, oxygen and sulfur, and optionally be substituted by 1-2 oxo groups;

R36, R37 H, $(C_1-C_8)$-alkyl;

R13, R14 independently of one another H, $(C_1-C_8)$-alkyl, hydroxy-$(C_1-C_4)$-alkyl, OH, $(C_1-C_4)$-alkoxy-$(C_1-C_4)$-alkyl;

R29, R30, R31 independently of one another H, $(C_1-C_8)$-alkyl, $(C_2-C_6)$-alkenyl, $(C_0-C_8)$-alkylene-aryl;

R32, R33 independently of one another H, $(C_1-C_6)$-alkyl or

R32 and R33 optionally together with the nitrogen atom to which they are bonded a 5-6 membered ring which, apart from the nitrogen atom, may also include 0-1 further heteroatoms from the group of NH, $N-(C_1-C_6)$-alkyl, oxygen and sulfur and optionally be substituted by 1-2 oxo groups;

R3 H, $(C_1-C_6)$-alkyl;

R4, R5 independently of one another H, $(C_1-C_6)$-alkyl, OH, $O-(C_1-C_6)$-alkyl, $O-CO(C_1-C_6)$-alkyl, $S-(C_1-C_6)$-alkyl;

R6, R7, R8, R9 independently of one another H, $(C_1-C_8)$-alkyl, or

R6 and R7, R8 and R9 independently of one another optionally oxo;

n, m independently of one another 0, 1, 2;

A, B, D, G independently of one another N, C(R38);

R38 H, F, Cl, Br, I, OH, $CF_3$, $NO_2$, CN, $OCF_3$, $O-(C_1-C_6)$-alkyl, $O(C_1-C_4)$-alkoxy-$(C_1-C_4)$-alkyl, $S-(C_1-C_6)$-alkyl, $(C_1-C_6)$-alkyl, $(C_2-C_6)$-alkenyl, $(C_3-C_8)$-cycloalkyl, $O-(C_3-C_8)$-cycloalkyl, $(C_3-C_8)$-cycloalkenyl, $O-(C_3-C_8)$-cycloalkenyl, $(C_2-C_6)$-alkynyl, $(C_0-C_8)$-alkylene-aryl, $O-(C_0-C_8)$-alkylene-aryl, S-aryl, N(R39)(R40), $SO_2-CH_3$, COOH, $COO-(C_1-C_6)$-alkyl, CON(R41)(R42), N(R43)CO(R44), $N(R45)SO_2(R46)$, CO(R47), $-(CR48R49)_x-O(R50)$;

R39, R40, R41, R42, R43, R45 independently of one another H, $(C_1-C_8)$-alkyl; or R39 and R40, R41 and R42 independently of one another optionally together with the nitrogen atom to which they are bonded a 5-6 membered ring which, apart from the nitrogen atom, may also include 0-1 further heteroatoms from the group of NH, $N-(C_1-C_6)$-alkyl, oxygen and sulfur;

R44, R46, R47 independently of one another H, $(C_1-C_8)$-alkyl, aryl;

R48, R49 independently of one another H, $(C_1-C_8)$-alkyl;

R50 H, $(C_1-C_6)$-alkyl;

x 1, 2, 3, 4;

Het five-membered aromatic heterocycle

X a bond, a group of the formula $-(CR51R52)_y$-in which one or more $-(CR51R52)$-groups may be replaced by Y to result in a chemically reasonable radical, C=C, C≡C;

Y O, S, N(R53), CO, SO, $SO_2$;

R51, R52 independently of one another H, $(C_1-C_4)$-alkyl, where R51 and R52 in the y groups may in each case have the same or different meanings;

y 1, 2, 3, 4, 5, 6;

R53 H, $(C_1-C_8)$-alkyl;

E 3-14 membered bivalent carbo- or heterocyclic ring structure having 0-4 heteroatoms from the group of N, O and S, which may optionally have substituents from the group of H, F, Cl, Br, I, OH, $CF_3$, $NO_2$, CN, $OCF_3$, oxo, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, N(R54)(R55), $SO_2$—$CH_3$, COOH, COO—$(C_1-C_6)$-alkyl, CON(R56)(R57), N(R58)CO(R59), N(R60)$SO_2$(R61), CO(R62) and be mono- or bicyclic;

R54, R55, R56, R57, R58, R60 independently of one another H, $(C_1-C_8)$-alkyl;

R54 and R55, R56 and R57 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R59, R61, R62 independently of one another H, $(C_1-C_8)$-alkyl, aryl;

K a bond, a group of the formula —(CR63R64)$_z$-in which one or more —(CR63R64)-groups may be replaced by Z to result in a chemically reasonable radical, C≡C, C=C;

Z O, S, N(R65), CO, SO, $SO_2$;

R63, R64 independently of one another H, $(C_1-C_8)$-alkyl, hydroxy, $(C_1-C_6)$-alkoxy, where R63 and R64 in the z groups may in each case have the same or different meanings;

z 1, 2, 3, 4, 5, 6; preferably 2, 3, 4, 5, 6;

R65 H, $(C_1-C_8)$-alkyl;

R11 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R66), CON(R67)(R68), hydroxy, hydroxy-$(C_1-C_4)$-alkyl, COO(R69), N(R70)CO$(C_1-C_6)$-alkyl, N(R71)(R72) or $SO_2CH_3$;

R66, R67, R68, R69, R70, R71, R72 independently of one another H, $(C_1-C_8)$-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur; or the N-oxides thereof and the physiologically tolerated salts thereof.

The invention relates to compounds of the formula I in the form of their racemates, enantiomer-enriched mixtures and pure enantiomers and to their diastereomers and mixtures thereof.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83 and R84 may be either straight-chain, branched or optionally halogenated.

In a further embodiment, the alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53, R54, R55, R56, R57, R58, R59, R60, R61, R62. R63, R64, R65, R66, R67, R68, R69, R70, R71, R72, R73, R74, R75, R76, R77, R78, R79. R80, R81, R82, R83 and R84 may be both straight-chain, branched and/or optionally substituted by substituents such as aryl, heteroaryl, alkoxy or halogen. This also applies if the alkyl, alkenyl and alkynyl radicals are part of another group, for example part of an alkoxy group (such as $(C_1-C_4)$-alkoxy-$(C_1-C_4)$-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n isomers of these radicals and branched isomers such as isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals such as aryl, heteroaryl, alkoxy or halogen. It is moreover possible for the additional substituents to occur in any position of the alkyl radical.

Cycloalkyl means for the purposes of the present application cycloalkyl and cycloalkyl-alkyl(alkyl which is substituted in turn by cycloalkyl, e.g. cyclopropylmethyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Optional possibilities are also polycyclic ring systems such as decalinyl, norbornanyl, bornanyl or adamantanyl. The cycloalkyl radicals may be unsubstituted or optionally substituted by one or more further radicals as listed above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 1-propynyl, 2-propynyl (propargyl), 1-butynyl, 2-butynyl or 3-butynyl.

Cycloalkenyl means for the purposes of the present application cycloalkenyl radicals and cycloalkenyl-alkyl radicals (alkyl which is substituted by cycloalkenyl), which comprise at least three carbon atoms. Examples of cycloalkenyl are: cyclopentenyl, cyclohexenyl, cycloheptenyl and cyclooctenyl. The alkenyl radicals and cycloalkenyl radicals may have one to three conjugated or unconjugated double bonds (thus also alk-dienyl and alk-trienyl radicals), preferably one double bond in a straight or branched chain. The same applies to the triple bonds in alkynyl radicals. The alkenyl and alkynyl radicals may be unsubstituted or optionally substituted by one or more further radicals as listed above by way of example for the alkyl radicals.

Aryl refers in the present invention to radicals derived from monocyclic or bicyclic aromatic compounds comprising no ring heteroatoms. Where aryl refers to systems which are not monocyclic, the saturated form (perhydroform) or the partially unsaturated form (for example the dihydroform or tetrahydroform) is also possible, where the respective forms are known and stable, for the second ring. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. Aryl is particularly preferably phenyl or naphthyl. The term "aryl" thus means in particular a phenyl or naphthyl group.

Heteroaryl radicals mean radicals derived from monocyclic or bicyclic aromatic compounds comprising ring heteroatoms, preferably N, O or S. Otherwise, the statements made about aryl radicals apply to heteroaryl radicals.

The aryl and heteroaryl radicals may be unsubstituted or substituted by one or more further radicals. Suitable further radicals are listed by way of example above for the alkyl radicals.

The compounds of the formula I may comprise one or more centers of asymmetry. The compounds of the formula I may therefore be in the form of their racemates, enantiomer-enriched mixtures, pure enantiomers, diastereomers and diastereomer mixtures. The present invention includes all these isomeric forms of the compounds of the formula I. These isomeric forms can be obtained by known methods even if not expressly described in some cases.

Mono-, bi- or spirocyclic rings may be saturated, partially saturated or unsaturated and also bridged.

C=C means a group of the formula R'C=CR" in which R' and R" are independently of one another H, $(C_1-C_8)$-alkyl, preferably H.

In the case where R1 and R2 together with the nitrogen atom to which they are bonded form a ring, this ring may be substituted by one or more of the substituents mentioned.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of the compounds according to the invention are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, trifluoromethanesulfonic, succinic, p-toluenesulfonic, tartaric and trifluoroacetic acids. The chloride salt is particularly preferably used for medical purposes. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion likewise fall within the scope of the invention as useful intermediates for preparing or purifying pharmaceutically acceptable salts and/or for use in nontherapeutic, for example in vitro, applications.

The term "physiologically functional derivative" used herein refers to any physiologically tolerated derivative of a compound according to the invention of the formula I, for example an ester, which is able on administration to a mammal such as, for example, a human to form (directly or indirectly) a compound of the formula I or an active metabolite thereof.

The physiologically functional derivatives also include prodrugs of the compounds according to the invention, as described, for example, in H. Okada et al., Chem. Pharm. Bull. 1994, 42, 57-61. Such prodrugs can be metabolized in vivo to a compound according to the invention. These prodrugs may themselves be active or not.

The compounds according to the invention may also exist in various polymorphous forms, for example as amorphous and crystalline polymorphous forms. All polymorphous forms of the compounds according to the invention lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

If radicals or substituents can occur more than once in the compounds of the formula I, they may all independently of one another have the stated meanings and be identical or different.

In a preferred embodiment, the meanings in the compounds of the formula I are

R1, R2 independently of one another H, $(C_1-C_8)$-alkyl, —(CR13R14)$_o$—R12, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, —CO—(CH$_2$)$_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, CF$_3$, NO$_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R22), CON(R23)(R24), hydroxy, COO(R25), N(R26)CO($C_1-C_6$)-alkyl or N(R27)(R28);

R12 OH, O—$(C_1-C_6)$-alkyl, CN, COO(R29), CON(R30)(R31), N(R32)(R33), 3-12 membered mono-, bi- or spirocyclic ring which may comprise one or more heteroatoms from the group of N, O and S, and the 3-12 membered ring may comprise further substituents such as F, Cl, Br, I, OH, CF$_3$, NO$_2$, CN, OCF$_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, $(C_2-C_6)$-alkynyl, O—$(C_0-C_8)$-alkylene-aryl, $(C_0-C_8)$-alkylene-aryl, N(R34)(R35), CO($C_1-C_6$)-alkyl and COO(R36); and R6, R7, R8, R9 independently of one another H, $(C_1-C_8)$-alkyl;

where the further radicals and groups in the compounds of the formula I have the meanings mentioned hereinbefore and preferred meanings mentioned hereinafter.

In a further preferred embodiment, the present invention relates to compounds of the formula I the meanings are:

R1, R2 independently of one another H, $(C_1-C_8)$-alkyl, —(CR13R14)$_o$—R12, $(C_1-C_4)$-alkoxy-$(C_1-C_4)$-alkyl, $(C_3-C_8)$-alkenyl, CO—$(C_1-C_8)$-alkyl, —CO—(CH$_2$)$_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, CF$_3$, $(C_1-C_6)$-alkyl, O—$(C_1-C_4)$-alkyl, $(C_1-C_4)$-alkoxy-$(C_1-C_4)$-alkyl, hydroxy-$(C_1-C_4)$- alkyl, (C$_0$-C$_2$)-alkylene-aryl, oxo, CO(R22), CON(R23)(R24), hydroxy, COO(R25), N(R26)CO(C$_1$-C$_6$)-alkyl, N(R27)(R28) or SO$_2$CH$_3$;

preferably independently of one another H, (C$_1$-C$_8$)-alkyl, —(CR13R14)$_o$—R12, (C$_1$-C$_4$)-alkoxy-(C$_1$-C$_4$)-alkyl, CO—(C$_1$-C$_8$)-alkyl, —CO—(CH$_2$)$_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono- or bicyclic ring which, apart from the nitrogen atom, may include 0 to 2 additional heteroatoms selected from the group of oxygen, nitrogen and sulfur, where the heterocyclic ring system may additionally be substituted by F, Cl, CF$_3$, (C$_1$-C$_6$)-alkyl, O—(C$_1$-C$_4$)-alkyl, (C$_1$-C$_4$)-alkoxy-(C$_1$-C$_4$)-alkyl, (C$_0$-C$_2$)-alkylene-aryl, oxo, CO(R22), hydroxy, N(R27)(R28) or SO$_2$CH$_3$;

particularly preferably independently of one another H, (C$_1$-C$_8$)-alkyl, —(CR13R14)$_o$—R12, (C$_1$-C$_4$)-alkoxy-(C$_1$-C$_4$)-alkyl, CO—(C$_1$-C$_8$)-alkyl, —CO—(CH$_2$)$_o$—R12, CO(C(R15)(R16))$_q$N(R17)(R18), or R1 and R2 form together with the nitrogen atom to which they are bonded a 4 to 10-membered mono- or bicyclic ring which, apart from the nitrogen atom, may include 0 to 2 additional heteroatoms selected from the group of oxygen and nitrogen, where the heterocyclic ring system may additionally be substituted by F, (C$_1$-C$_6$)-alkyl, (C$_1$-C$_4$)-alkoxy-(C$_1$-C$_4$)-alkyl, oxo, CO(R22), hydroxy, N(R27)(R28);

o 0, 1, 2, 3, 4, 5, 6; preferably 0, 1, 2, 3, 4; particularly preferably 0, 1, 2, 3;

q 1, 2, 3; preferably 1 or 2;

s 0, 1, 2, 3, 4; preferably 0, 1, 2, 3; particularly preferably 0, 1, 2;

R15, R16, R17, R18, R19, R20, R21, R22, R23, R24, R25, R26, R27, R28 independently of one another H, (C$_1$-C$_6$)-alkyl; or R17 and R18, R23 and R24, R27 and R28 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur; the ring is preferably pyrrolidine, piperidine, N-methylpiperazine, morpholine;

R12 OH, O—(C$_1$-C$_6$)-alkyl, CN, COO(R29), CON(R30)(R31), 3-12 membered mono-, bi- or spirocyclic ring which may comprise one or more heteroatoms from the group of N, O and S, and the 3-12 membered ring may comprise further substituents such as F, Cl, Br, OH, CF$_3$, CN, oxo, O—(C$_1$-C$_6$)-alkyl, (C$_1$-C$_4$)-alkoxy-(C$_1$-C$_4$)-alkyl, (C$_1$-C$_6$)-alkyl, O—(C$_0$-C$_8$)-alkylene-aryl, (C$_0$-C$_8$)-alkylene-aryl, N(R34)(R35), CO(C$_1$-C$_6$)-alkyl, COO(R36), S(O)$_u$(R37);

preferably OH, O—(C$_1$-C$_6$)-alkyl, CN, 3-10 membered mono- or bicyclic ring which may comprise 1-3 heteroatoms from the group of N, O and S, and the 3-10 membered ring may comprise further substituents such as F, Cl, Br, OH, CF$_3$, CN, oxo, O—(C$_1$-C$_6$)-alkyl, (C$_1$-C$_4$)-alkoxy-(C$_1$-C$_4$)-alkyl, (C$_1$-C$_6$)-alkyl, (C$_0$-C$_2$)-alkylene-aryl, N(R34)(R35), CO(C$_1$-C$_6$)-alkyl;

particularly preferably OH, O—(C$_1$-C$_6$)-alkyl, 3-10 membered mono- or bicyclic ring which may comprise 1-2 heteroatoms from the group of N, O and S, and the 3-10 membered ring may comprise further substituents such as F, OH, oxo, (C$_1$-C$_6$)-alkyl, CO(C$_1$-C$_6$)-alkyl;

u 0, 1, 2; preferably 0 or 2; particularly preferably 2;

R34, R35 independently of one another H, (C$_1$-C$_8$)-alkyl; or

R34 and R35 optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur, and optionally be substituted by 1-2 oxo groups;

R36, R37 H, (C$_1$-C$_8$)-alkyl;

R13, R14 independently of one another H, (C$_1$-C$_8$)-alkyl, hydroxy-(C$_1$-C$_4$)-alkyl, OH, (C$_1$-C$_4$)-alkoxy-(C$_1$-C$_4$)-alkyl;

R29, R30, R31 independently of one another H, (C$_1$-C$_8$)-alkyl;

R3 H, (C$_1$-C$_6$)-alkyl; preferably H;

R4, R5 independently of one another H, (C$_1$-C$_6$)-alkyl, OH, O—(C$_1$-C$_6$)-alkyl, O—CO(C$_1$-C$_6$)-alkyl, S—(C$_1$-C$_6$)-alkyl; preferably independently of one another H, (C$_1$-C$_6$)-alkyl, OH, O—(C$_1$-C$_6$)-alkyl, O—CO(C$_1$-C$_6$)-alkyl; particularly preferably independently of one another H, OH, O—(C$_1$-C$_6$)-alkyl, very particularly preferably H;

R6, R7, R8, R9 H; or

R6 and R7, R8 and R9 independently of one another optionally oxo;

R6, R7, R8, R9 are preferably H;

n 1 m 1 or 2; preferably 1;

A, B, D, G independently of one another N, C(R38); or the groups A and B or D and G are in each case C(R38) and together form an ortho-phenylene unit so that the overall result is a 1,4-bisubstituted naphthalene system;

preferably A, B, G and D are independently of one another N, C(R38); particularly preferably D and G are C(R38) and either A or B is N, with the respective other group B or A being C(R38); very particularly preferably B is N, C(R38); and A, D, G C(R38);

especially preferably

A, B, D, G are C(R38);

R38 H, F, Cl, Br, CF$_3$, CN, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_0$-C$_8$)-alkylene-aryl, O—(C$_0$-C$_8$)-alkylene-aryl, N(R39)(R40), SO$_2$—CH$_3$, CON(R41)(R42), N(R43)CO(R44), CO(R47), —(CR48R49)$_n$—O(R50);

preferably H, F, Cl, Br, CF$_3$, CN, O—(C$_1$-C$_6$)-alkyl, (C$_1$-C$_6$)-alkyl, SO$_2$—CH$_3$, CON(R41)(R42), N(R43)CO(R44), CO(R47), —(CR48R49)$_x$—O(R50);

particularly preferably H, F, Cl, CF$_3$, CN, (C$_1$-C$_6$)-alkyl, —(CR48R49)$_x$—O(R50);

R39, R40, R41, R42, R43 independently of one another H, (C$_1$-C$_8$)-alkyl; or

R39 and R40, R41 and R42 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;

R44, R47 independently of one another H, (C$_1$-C$_8$)-alkyl, aryl; preferably independently of one another H, (C$_1$-C$_8$)-alkyl;

R48, R49 H;

R50 H, (C$_1$-C$_6$)-alkyl;

x 1, 2; preferably 1;

Het five-membered aromatic heterocycle, preferably

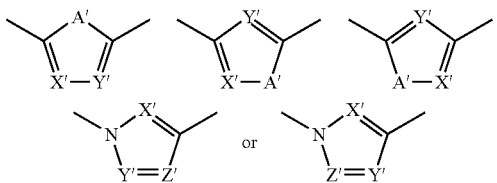

in which

A' is O, S, NR73,

X', Y' and Z' are independently of one another CR74 or N, and

R73, R74 are independently of one another H, $(C_1-C_8)$-alkyl;

Het is particularly preferably selected from the group consisting of oxadiazoles, thiadiazoles, thiazoles, oxazoles, triazoles, thiophenes, furans and pyrroles; Het is very particularly preferably selected from oxadiazoles, thiadiazoles, thiazoles and oxazoles;

X a bond, a group of the formula $—(CR51R52)_v$-in which one or more —(CR51R52)-groups may be replaced by Y to result in a chemically reasonable radical, C=C, C≡C; preferably a bond, $CH_2—CH_2$, $CH_2Y$, $YCH_2$, (R75) $YCH_2$, $CH_2—NCO(R75)$, $CH_2CON(R75)$; C(R76)(R77), C(R78)(R79)O, N(R75), C=C, C≡C; particularly preferably a bond, $CH_2—CH_2$, C(R76)(R77), N(R75), $CH_2Y$, $CH_2Y(R75)$, $CH_2—NCO(R75)$, $CH_2CON(R75)$; C=C; very particularly preferably a bond, $CH_2—CH_2$, C(R76) (R77), C=C, (R75)$YCH_2$, $CH_2—NCO(R75)$;

Y O, S, N(R53), CO; preferably O, S, N(R53);

R53 H, $(C_1-C_8)$-alkyl;

R75, R76, R77, R78, R79 independently of one another H, $(C_1-C_8)$-alkyl;

E 3-8 membered bivalent carbo- or heterocyclic ring structure having 0-4 heteroatoms from the group of N, O and S, which may optionally have substituents from the group of H, F, Cl, Br, OH, $CF_3$, $NO_2$, CN, $OCF_3$, $O—(C_1-C_6)$-alkyl, $O—(C_1-C_4)$-alkoxy-$(C_1-C_4)$-alkyl, $S—(C_1-C_6)$-alkyl, $(C_1-C_6)$-alkyl, $(C_2-C_6)$-alkenyl, $O—(C_3-C_8)$-cycloalkyl, $(C_2-C_6)$-alkynyl, $(C_0-C_8)$-alkylene-aryl, $O—(C_0-C_8)$-alkylene-aryl, S-aryl, N(R54)(R55), $SO_2—CH_3$, N(R58)CO(R59), N(R60)$SO_2$(R61), CO(R62) and be mono- or bicyclic;

preferably 5-7 membered bivalent carbo- or heterocyclic ring structure having 0-3 heteroatoms from the group of N, O and S, which may optionally have substituents from the group of H, F, Cl, Br, OH, $CF_3$, $NO_2$, CN, $OCF_3$, $O—(C_1-C_6)$-alkyl, $S—(C_1-C_6)$-alkyl, $(C_1-C_6)$-alkyl, $(C_2-C_6)$-alkenyl, $O—(C_0-C_8)$-alkylene-aryl, S-aryl, N(R54)(R55), $SO_2—CH_3$, N(R58)CO(R59), CO(R62) and be mono- or bicyclic;

particularly preferably 5-7 membered bivalent carbo- or heterocyclic ring structure having 0-2 heteroatoms from the group of N, O and S, which may optionally have substituents from the group of H, F, Cl, Br, OH, $CF_3$, $NO_2$, $OCF_3$, $O—(C_1-C_6)$-alkyl, $(C_1-C_6)$-alkyl, $(C_2-C_6)$-alkenyl, N(R54)(R55), $SO_2—CH_3$, CO(R62), and which is very particularly preferably monocyclic;

e.g. E is benzene, pyridine, pyrimidine, piperidine, pyrrolidine, cyclopentane, cyclohexane, piperazine, homopiperazine, thiazole, thiophene, furan, pyrrole, pyrazole, 1,2,3,6-tetrahydropyridine, 4,5-dihydroisoxazole, oxazole;

R54, R55, R58, R60 independently of one another H, $(C_1-C_8)$-alkyl;

R59, R61, R62 independently of one another H, $(C_1-C_8)$-alkyl, aryl; preferably independently of one another H, $(C_1-C_8)$-alkyl;

K O, a bond, $CH_2O$, $OCH_2$, S, SO, $SO_2$, N(R80), N(R81) CO, CON(R82), $(C(R83)(R84))_v$, CO, C=C, C≡C, $SCH_2$, $SO_2CH_2$; preferably O, a bond, $CH_2O$, $OCH_2$, N(R80), N(R81)CO, CON(R82), $(C(R83)(R84))_v$, CO, C≡C, $SCH_2$; particularly preferably O, a bond, $CH_2O$, $OCH_2$, CON(R82), $(C(R83)(R84))_v$, CO, C≡C;

v 1, 2, 3, 4; preferably 1, 2, 3; particularly preferably 1, 2;

R80, R81, R82, R83, R84 independently of one another H, $(C_1-C_8)$-alkyl;

R11 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, $CF_3$, CN, $(C_1-C_6)$-alkyl, $O—(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R66), CON(R67) (R68), hydroxy, COO(R69), N(R70)CO$(C_1-C_6)$-alkyl, N(R71)(R72) or $SO_2CH_3$;

preferably $(C_1-C_8)$-alkyl, $(C_1-C_4)$-alkoxy-$(C_1-C_4)$-alkyl, a 3 to 10-membered mono-, bi- or spirocyclic ring which may include 0 to 3 heteroatoms selected from the group of oxygen, nitrogen and sulfur, where the ring system may additionally be substituted by F, Cl, Br, $CF_3$, CN, $(C_1-C_6)$-alkyl, $O—(C_1-C_8)$-alkyl, $(C_0-C_2)$-alkylene-aryl, oxo, CO(R66), CON(R67)(R68), hydroxy, N(R70)CO$(C_1-C_6)$-alkyl, N(R71)(R72) or $SO_2CH_3$;

particularly preferably $(C_1-C_8)$-alkyl, $(C_1-C_4)$-alkoxy-$(C_1-C_4)$-alkyl, a 3 to 10-membered mono- or bicyclic ring which may include 0 to 2 heteroatoms selected from the group of oxygen, nitrogen and sulfur, where the ring system may additionally be substituted by F, Cl, Br, $CF_3$, CN, $(C_1-C_6)$-alkyl, $O—(C_1-C_8)$-alkyl, oxo, CO(R66), CON(R67)(R68), N(R70)CO$(C_1-C_6)$-alkyl, or $SO_2CH_3$;

R66, R67, R68, R69, R70, R71, R72 independently of one another H, $(C_1-C_8)$-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur; or the N-oxides thereof and the physiologically tolerated salts thereof.

In a preferred embodiment of the invention, the radicals R1, R2, R11, R38 and groups X, E, K have the following meanings:

R1, R2 independently of one another H, $(C_1-C_8)$-alkyl, $—(CR13R14)_o—R12$, $(C_1-C_4)$-alkoxy-$(C_1-C_4)$-alkyl, or R1 and R2 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by $(C_1-C_6)$-alkyl, $O—(C_1-C_4)$-alkyl, $(C_1-C_4)$-alkoxy-$(C_1-C_4)$-alkyl, hydroxy-$(C_1-C_4)$-alkyl, $(C_0-C_2)$-alkylene-aryl, oxo, CO(R22), CON(R23)(R24), hydroxy, N(R27)(R28) or $SO_2CH_3$;

preferably independently of one another H, (C₁-C₈)-alkyl, —(CR13R14)ₒ—, R12, (C₁-C₄)-alkoxy-(C₁-C₄)-alkyl, or R1 and R2 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by (C₁-C₆)-alkyl, O—(C₁-C₄)-alkyl, (C₁-C₄)-alkoxy-(C₁-C₄)-alkyl, hydroxy-(C₁-C₄)-alkyl, (C₀-C₂)-alkylene-aryl, oxo, CO(R22), CON(R23)(R24), hydroxy or N(R27)(R28);

very particularly preferably independently of one another H, (C₁-C₈)-alkyl, or R1 and R2 form together with the nitrogen atom to which they are bonded a 5 to 6-membered monocyclic ring which, apart from the nitrogen atom, may include 0 to 1 additional heteroatoms selected from the group of oxygen, nitrogen and sulfur, where the heterocyclic ring system may additionally be substituted by (C₁-C₆)-alkyl;

especially preferably independently of one another H, (C₁-C₈)-alkyl;

o 0, 1, 2, 3, 4;

R22, R23, R24, R27, R28 independently of one another H, (C₁-C₆)-alkyl; or

R23 and R24, R27 and R28 independently of one another optionally together with the nitrogen atom to which they are bonded a 5-6 membered ring which, apart from the nitrogen atom, may also include 0-1 further heteroatoms from the group of NH, N—(C₁-C₆)-alkyl, oxygen and sulfur;

R12 OH, O—(C₁-C₆)-alkyl, CN, 3-12 membered mono-, bi- or spirocyclic ring which may comprise 1 to 3 heteroatoms from the group of N, O and S, and the 3-12 membered ring may comprise further substituents such as F, OH, CF₃, CN, oxo, (C₁-C₆)-alkyl, (C₀-C₂)-alkylene-aryl, N(R34)(R35), COO(R36), CO(C₁-C₆)-alkyl;

R34, R35 independently of one another H, (C₁-C₄)-alkyl;

R36 H, (C₁-C₆)-alkyl;

R13, R14 independently of one another H, (C₁-C₈)-alkyl, hydroxy-(C₁-C₄)-alkyl, OH, (C₁-C₄)-alkoxy-(C₁-C₄)-alkyl;

R38 H, F, Cl, Br, CF₃, CN, (C₁-C₆)-alkyl;

X a bond, CH₂CH₂, C(R76)(R77), N(R75), C≡C, (R75)YCH₂, CH₂—NCO(R75), CH₂CON(R75);

Y O, S, N(R53), CO

R75, R76, R77 independently of one another H, (C₁-C₈)-alkyl;

R53 H, (C₁-C₈)-alkyl;

E 5-7 membered bivalent carbo- or heterocyclic ring structure having 0-3 heteroatoms from the group of N, O and S, which may optionally have substituents from the group of H, F, Cl, Br, CF₃, OH, CN, OCF₃, O—(C₁-C₆)-alkyl, (C₁-C₆)-alkyl, SO₂—CH₃, CO(R65);

R65 H, (C₁-C₈)-alkyl;

K O, a bond, CH₂O, CH₂, OCH₂, S, SO₂, N(R80), N(R81)CO, CON(R82), (C(R83)(R84))ᵥ, CO, C≡C, SCH₂, SO₂CH₂; preferably O, a bond, CH₂O, CH₂, OCH₂, N(R80), C≡C;

v 1, 2, 3;

R80, R81, R82, R83, R84 independently of one another H, (C₁-C₈)-alkyl;

R11 (C₁-C₈)-alkyl, (C₁-C₄)-alkoxy-(C₁-C₄)-alkyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, CF₃, CN, (C₁-C₆)-alkyl, O—(C₁-C₈)-alkyl, oxo, CO(R66), hydroxy, N(R70)CO(C₁-C₆)-alkyl, or SO₂CH₃;

R66, R70 independently of one another H, (C₁-C₈)-alkyl;

the N-oxides thereof and the physiologically tolerated salts thereof.

Particularly preferred compounds of the formula I are those in which

A, B, D, G are independently of one another N or C(R38), and the total number of nitrogen atoms in this ring is 0-2, preferably 0 or 1, and in the case where the total number of nitrogen atoms is 1, particularly preferably A or B are N, and very particularly preferably B is N.

Very particularly preferred compounds of the formula I are those in which n is 1 and m is 1 or 2.

Especially preferred compounds of the formula I are those in which

A, B, D, G are independently of one another N or C(R38), and the total number of nitrogen atoms in this ring is 0-2, preferably 0 or 1, and in the case where the total number of nitrogen atoms is 1, particularly preferably A or B are N, and very particularly preferably B is N.

n is 1 and m is 1 or 2.

The radical R38 has the aforementioned meanings.

Especially preferred compounds of the formula I are those in which

Het is selected from the group consisting of oxadiazoles, thiadiazoles, thiazoles, oxazoles, triazoles, thiophenes, furans and pyrroles; Het is very particularly preferably selected from oxadiazoles, thiadiazoles, thiazoles and oxazoles.

The further radicals may have the aforementioned meanings in the aforementioned preferred embodiments.

In a very particularly preferred embodiment, the present application relates to compounds of the formula IA

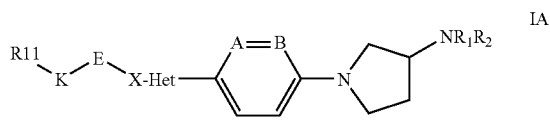

in which the meanings are

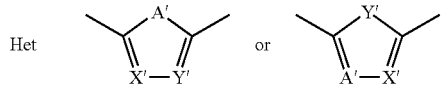

in which

A' is O, S,

X' and Y' are independently of one another CR74 or N, and

R74 are independently of one another H, (C₁-C₈)-alkyl;

A, B are CH or CF, where in the case of CF only one of the two groups A or B is CF and the other group is CH;

R1, R2 independently of one another H, (C₁-C₈)-alkyl, —(CR13R14)ₒ—R12, (C₁-C₄)-alkoxy-(C₁-C₄)-alkyl, (C₃-C₈)-alkenyl, (C₃-C₈)-alkynyl, CO—(C₁-C₈)-alkyl, —CO—(CH₂)ₒ—R12, CO(C(R15)(R16))qN(R17)(R18), CO(C(R19)(R20))ₛO(R21); or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R22), CON(R23)(R24), hydroxy, COO(R25), N(R26)CO$(C_1-C_6)$-alkyl, N(R27)(R28) or $SO_2CH_3$;

particularly preferably independently of one another H, $(C_1-C_8)$-alkyl, —(CR13R14)$_o$—R12, $(C_1-C_4)$-alkoxy-$(C_1-C_4)$-alkyl, CO—$(C_1-C_8)$-alkyl, —CO—$(CH_2)_o$—R12; or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R22), CON(R23)(R24), hydroxyl, N(R26)CO$(C_1-C_6)$-alkyl, N(R27)(R28);

very particularly preferably independently of one another H, $(C_1-C_8)$-alkyl, —(CR13R14)$_o$—R12, $(C_1-C_4)$-alkoxy-$(C_1-C_4)$-alkyl, —CO—$(CH_2)_o$—R12; or R1 and R2 form together with the nitrogen atom to which they are bonded a 4 to 7-membered monocyclic ring which, apart from the nitrogen atom, may include 0 to 2 additional heteroatoms selected from the group of oxygen, nitrogen and sulfur, where the heterocyclic ring system may additionally be substituted by F, Cl, $CF_3$, $(C_1-C_6)$-alkyl, O—$(C_1-C_8)$-alkyl, hydroxy-$(C_1-C_4)$-alkyl, CO(R22), CON(R23)(R24), hydroxy, N(R26)CO$(C_1-C_6)$-alkyl, N(R27)(R28);

especially preferably independently of one another H, $(C_1-C_8)$-alkyl, or R1 and R2 form together with the nitrogen atom to which they are bonded a 5 to 6-membered monocyclic ring which, apart from the nitrogen atom, may include 0 to 1 additional heteroatoms selected from the group of oxygen, nitrogen and sulfur, where the heterocyclic ring system may additionally be substituted by $(C_1-C_6)$-alkyl;

further very particularly preferably independently of one another H, $(C_1-C_8)$-alkyl;

o 0, 1, 2, 3, 4, 5, 6; preferably 0, 1, 2, 3, 4;

q, s independently of one another 0, 1, 2, 3, 4;

R15, R16, R17, R18, R19, R20, R21, R22, R23, R24, R25, R26, R27, R28 independently of one another H, $(C_1-C_6)$-alkyl;

R17 and R18, R23 and R24, R27 and R28 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R12 OH, O—$(C_1-C_6)$-alkyl, CN, COO(R29), CON(R30)(R31), N(R32)(R33), 3-12 membered mono-, bi- or spirocyclic ring which may comprise one or more heteroatoms from the group of N, O and S, and the 3-12 membered ring may comprise further substituents such as F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, $(C_2-C_6)$-alkynyl, O—$(C_0-C_8)$-alkylene-aryl, $(C_0-C_8)$-alkylene-aryl, N(R34)(R35), CO$(C_1-C_6)$-alkyl, COO(R36) and S(O)$_u$(R37); particularly preferably OH, O—$(C_1-C_6)$-alkyl, CN, CON(R30)(R31), N(R32)(R33), 3-7 membered monocyclic ring which may comprise one or more heteroatoms from the group of N, O and S, and the 3-7 membered ring may comprise further substituents such as F, Cl, OH, $CF_3$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, $(C_2-C_6)$-alkynyl, O—$(C_0-C_8)$-alkylene-aryl, $(C_0-C_8)$-alkylene-aryl, N(R34)(R35) and CO$(C_1-C_6)$-alkyl;

u 0, 1, 2;

R34, R35 independently of one another H, $(C_1-C_8)$-alkyl;

R34 and R35 optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur and optionally be substituted by 1-2 oxo groups;

R36, R37 H, $(C_1-C_8)$-alkyl;

R13, R14 independently of one another H, $(C_1-C_8)$-alkyl, hydroxy-$(C_1-C_4)$-alkyl, OH, $(C_1-C_4)$-alkoxy-$(C_1-C_4)$-alkyl;

R29, R30, R31 independently of one another H, $(C_1-C_8)$-alkyl, $(C_2-C_6)$-alkenyl, $(C_0-C_8)$-alkylene-aryl;

R32, R33 independently of one another H, $(C_1-C_6)$-alkyl or

R32 and R33 optionally together with the nitrogen atom to which they are bonded a 5-6 membered ring, which apart from the nitrogen atom, may also include 0-1 further heteroatoms from the group of NH, N—$(C_1-C_6)$-alkyl, oxygen and sulfur and optionally be substituted by 1-2 oxo groups;

X a bond, a group of the formula —(CR51R52)$_y$-in which one or more —(CR51R52)-groups may be replaced by Y to result in a chemically reasonable radical, C=C, C≡C; preferably a bond, $CH_2$—$CH_2$, $CH_2$Y, Y$CH_2$, (R75)Y$CH_2$, $CH_2$—NCO(R75), $CH_2$CON(R75); C(R76)(R77), C(R78)(R79)O, N(R75), C=C, C≡C; particularly preferably a bond, $CH_2$—$CH_2$, C(R76)(R77), N(R75), $CH_2$Y, $CH_2$Y(R75), $CH_2$—NCO(R75), $CH_2$CON(R75); C=C; very particularly preferably a bond, $CH_2$—$CH_2$, C(R76)(R77), C=C; (R75)Y$CH_2$, $CH_2$—NCO(R75);

Y O, S, N(R53), CO, SO, $SO_2$; particularly preferably O, S, N(R53), CO; very particularly preferably O, N(R53);

R51, R52 independently of one another H, $(C_1-C_4)$-alkyl, where R51 and R52 in the y groups in each case can have the same or different meanings;

y 1, 2, 3, 4, 5, 6;

R53 H, $(C_1-C_8)$-alkyl;

E 3-14 membered bivalent carbo- or heterocyclic ring structure having 0-4 heteroatoms from the group of N, O and S, which may optionally have substituents from the group of H, F, Cl, Br, I, OH, $CF_3$, $NO_2$, CN, $OCF_3$, oxo, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_2-C_6)$-alkynyl, $(C_0-C_8)$-alkylene-aryl, O—$(C_0-C_8)$-alkylene-aryl, S-aryl, N(R54)(R55), $SO_2$—$CH_3$, COOH, COO—$(C_1-C_6)$-alkyl, CON(R56)(R57), N(R58)CO(R59), N(R60)$SO_2$(R61), CO(R62) and be mono- or bicyclic;

preferably 5-7 membered bivalent carbo- or heterocyclic ring structure having 0-3 heteroatoms from the group of N, O and S, which may optionally have substituents from the group of H, F, Cl, OH, CN, $CF_3$, $OCF_3$, O—$(C_1-C_6)$-alkyl, $(C_1-C_6)$-alkyl, $(C_0-C_8)$-alkylene-aryl, O—$(C_3-C_8)$-cycloalkyl, N(R54)(R55), $SO_2$—$CH_3$, CON(R56)(R57), N(R58)CO(R59), N(R60)$SO_2$(R61), CO(R62) and be mono- or bicyclic; particularly preferably 5-7 membered bivalent carbo- or heterocyclic ring structure having 0-3 heteroatoms from the group of N, O and S, which may optionally have substituents from the group of H, F, Cl, CF$_3$, OCF$_3$, O—(C$_1$-C$_6$)-alkyl, (C$_1$-C$_6$)-alkyl, (C$_0$-C$_2$)-alkylene-aryl, O—(C$_3$-C$_6$)-cycloalkyl, N(R54)(R55), CON (R56)(R57), N(R58)CO(R59), CO(R62) and be mono- or bicyclic;

R54, R55, R56, R57, R58, R60 independently of one another H, (C$_1$-C$_8$)-alkyl;

R54 and R55, R56 and R57 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;

R59, R61, R62 independently of one another H, (C$_1$-C$_8$)-alkyl, aryl;

K a bond, a group of the formula —(CR63R64)$_z$—, in which one or more —(CR63R64)-groups may be replaced by Z to result in a chemically reasonable radical, C≡C, C=C; preferably O, a bond, CH$_2$O, CH$_2$, OCH$_2$, S, SO$_2$, N(R80), N(R81)CO, CON(R82), (C(R83)(R84))$_v$, CO, C≡C, SCH$_2$, SO$_2$CH$_2$;

Z O, S, N(R65), CO, SO, SO$_2$;

R63, R64 independently of one another H, (C$_1$-C$_8$)-alkyl, hydroxy, (C$_1$-C$_6$)-alkoxy, where R63 and R64 in the z groups may in each case have the same or different meanings;

z 1, 2, 3, 4, 5, 6, preferably 2, 3, 4, 5, 6;

R65 H, (C$_1$-C$_8$)-alkyl;

R11 H, (C$_1$-C$_8$)-alkyl, (C$_1$-C$_4$)-alkoxy-(C$_1$-C$_4$)-alkyl, (C$_3$-C$_8$)-alkenyl, (C$_3$-C$_8$)-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, (C$_0$-C$_8$)-alkylene-aryl, oxo, CO(R66), CON(R67)(R68), hydroxy, hydroxy-(C$_1$-C$_4$)-alkyl, COO(R69), N(R70)CO(C$_1$-C$_6$)-alkyl, N(R71)(R72) or SO$_2$CH$_3$;

preferably H, (C$_1$-C$_8$)-alkyl, (C$_1$-C$_4$)-alkoxy-(C$_1$-C$_4$)-alkyl, a 5 to 6-membered monocyclic ring which may include 0 to 3 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, CO(R66), CON(R67)(R68), hydroxy, N(R70)CO(C$_1$-C$_6$)-alkyl, N(R71)(R72) or SO$_2$CH$_3$;

particularly preferably H, (C$_1$-C$_8$)-alkyl, (C$_1$-C$_4$)-alkoxy-(C$_1$-C$_4$)-alkyl, a 5 to 6-membered monocyclic ring which may include 0 to 2 heteroatoms selected from the group of oxygen, nitrogen and sulfur, where the ring system may additionally be substituted by F, Cl, Br, CF$_3$, NO$_2$, CN, (C$_1$-C$_6$)-alkyl or O—(C$_1$-C$_8$)-alkyl;

R66, R67, R68, R69, R70, R71, R72 independently of one another H, (C$_1$-C$_8$)-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur; or the N-oxides thereof and the physiologically tolerated salts thereof.

The compounds of the invention of the formula I and their precursors can be prepared by processes known to the skilled worker.

The preparation of compounds of the invention of the formula I is described below for the example of the preparation of [1,3,4]-oxadiazoles (Ia), [1,3,4]-thiadiazoles (Ib) and [1,2,4]-oxadiazoles (Ic):

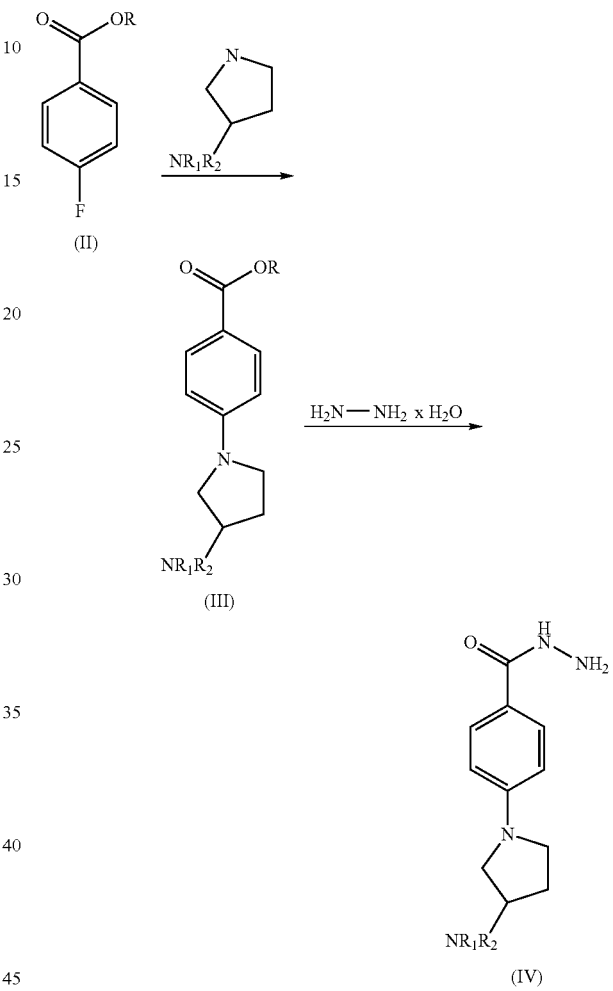

in which
R is H, (C$_1$-C$_8$)-alkyl, and
R1 and R2 have the aforementioned meanings;

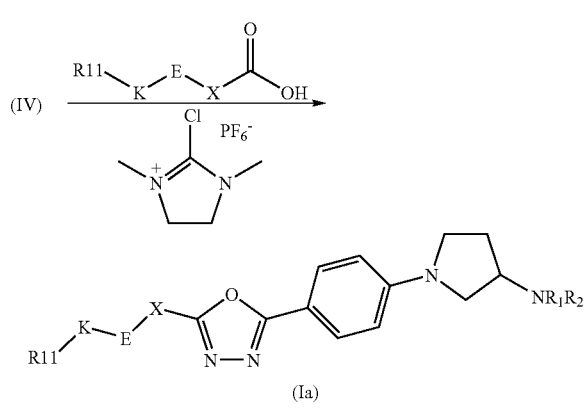

or Burgess' reagent

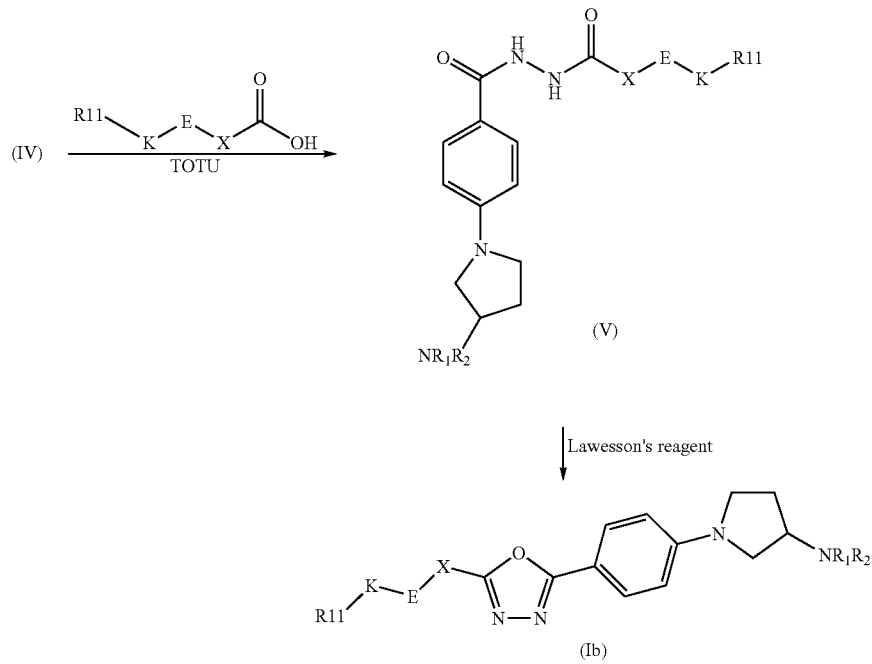
in which R1, R2, R11 and X, E and K have the aforementioned meanings.
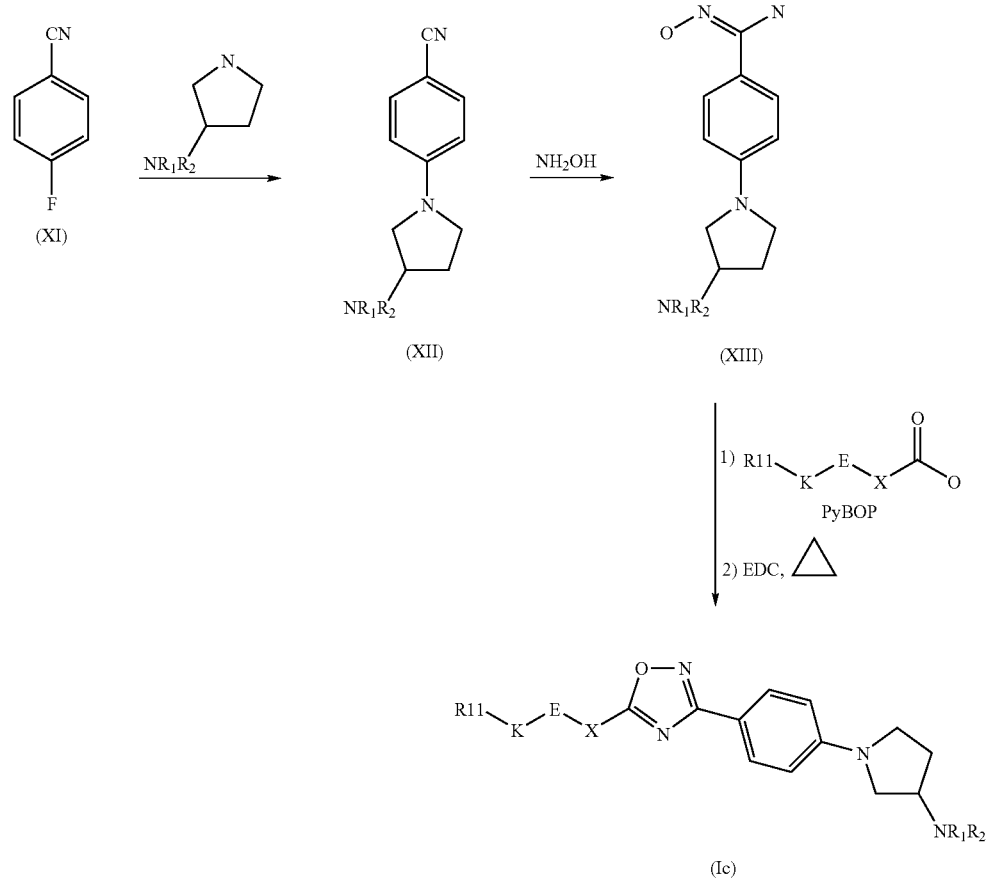

in which R1, R2, R11 and X, E and K have the aforementioned meanings.

Use

This invention further relates to the use of compounds of the formula I and their pharmaceutical compositions as MCH receptor ligands. The MCH receptor ligands of the invention are particularly suitable as modulators of the activity of the MCH1R.

The role of MCH in regulating the energy balance has now been well documented (Qu, D. et al.; Nature 1996, 380, 243-7; Shimada, M. et al. Nature 1998, 396, 670-4; Chen, Y. et al. Endocrinology 2002, 143, 2469-77; Endocrinology 2003, 144, 4831-40; Review: G. Hervieu, Expert Opin. Ther. Targets 2003, 7, 495-511).

There are also indications that MCH antagonists can have a beneficial influence on centrally related disorders such as, for example, depression (Borowsky, B. et al.; Nature Medicine 2002, 8, 825-30; Review: G. Hervieu, Expert Opin. Ther. Targets 2003, 7, 495-511).

Compounds of this type are particularly suitable for the treatment and/or prevention of
1. Obesity
2. Diabetes mellitus, especially type 2 diabetes, including the prevention of the sequelae associated therewith.
Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc., especially those (but not restricted thereto) which are characterized by one or more of the following factors:
   high plasma triglyceride concentrations, high postprandial plasma triglyceride concentrations,
   low HDL cholesterol concentration
4. Various other conditions which may be associated with the metabolic syndrome, such as:
   thromboses, hypercoagulable and prothrombotic stages (arterial and venous)
   high blood pressure
   heart failure such as, for example (but not restricted thereto), following myocardial infarction, hypertensive heart disease or cardiomyopathy
5. Psychiatric indications such as
   depression
   anxiety states
   disturbances of the circadian rhythm
   affection disorders
   schizophrenia
   addictive disorders Formulations The amount of a compound of formula (I) which is necessary to achieve the desired biological effect depends on a number of factors, for example the specific compound chosen, the intended use, the mode of administration and the clinical condition of the patient. In general, the daily dose is in the range from 0.001 mg to 100 mg, preferably from 0.3 mg to 100 mg (typically from 0.01 mg to 50 mg, preferably from 3 mg to 50 mg) per day per kilogram of body weight, for example 0.1-10 mg/kg/day, preferably 3-10 mg/kg/day. An intravenous dose may be, for example, in the range from 0.001 mg to 1.0 mg/kg, preferably from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Single doses may contain, for example, from 1 mg to 10 g of the active ingredient. It is thus possible for ampoules for injections to contain, for example, from 1 mg to 100 mg, and for single-dose formulations which can be administered orally, such as, for example, tablets or capsules, to contain, for example, from 0.05 to 1000 mg, typically from 0.5 to 600 mg, or in a further embodiment from 1.0 to 1000 mg, typically from 10 to 600 mg. In the case of pharmaceutically acceptable salts, the aforementioned weight data are based on the weight of the salt of the underlying free compound. For the prophylaxis or therapy of the abovementioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as a single dose, for example as a tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2(6): 318 (1986) by electrotransport or iontophoresis.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects.

The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

In a further aspect of the invention, the compounds of the formula I can be administered in combination with one or more other pharmacologically active substances which have, for example, favorable effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further pharmacologically active substances suitable in particular are:

Antidiabetics

All antidiabetics mentioned in the Rote Liste 2001, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Suitable antidiabetics include all insulins and insulin derivatives such as, for example, Lantus® or HMR 1964 or Apidra®, and other fast-acting insulins (see, e.g., U.S. Pat. No. 6,221,633), amylin, GLP-1 and GLP-2 derivatives such as described in WO 01/04146 or else such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon receptor antagonists, GLP-1 agonists, DPP-IV inhibitors, potassium channel openers such as, for example, those disclosed in WO 97/26265 and WO 99/03861 of Novo Nordisk A/S, insulin sensitizers, activators of insulin receptor kinase, inhibitors of GSK3-beta, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism and lead to a change in the lipid composition of the blood, such as antihyperlipidemic active ingredients and antilipidemic active ingredients, e.g. HMGCoA reductase inhibitors, inhibitors of cholesterol transport/of cholesterol uptake, inhibitors of bile acid reabsorption or inhibitors of microsomal triglyceride transfer protein (MTP), compounds which reduce food intake and/or food absorption, PPAR and RXR agonists and active ingredients which act on the ATP-dependent potassium channel of the beta cells.

In one embodiment of the invention, the present compounds are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3, 4-dihydro-3-methyl-4-oxo-2-quinazolinylmethoxy]phenyl] methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. No. 6,245,744, U.S. Pat. No. 6,221,897, U.S. Pat. No. 6,277,831, EP 0 683 773, EP 0 683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6); Caromax is a carob-containing product from Nutrinova, Nutrition Specialties & Food Ingredients GmbH, Industriepark Hoechst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In another embodiment, the further active ingredient is rimonabant.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6, 7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea; hydrochloride (SB-334867-A)), CB1 antagonists/ inverse agonists, H3 antagonists/inverse agonists (e.g. 3-cyclohexyl-1-(4,4-dimethyl-1,4,6,7-tetrahydroimidazo[4,5-c] pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramines), mixed serotoninergic and noradrenergic compounds (e.g. WO 00/71549), 5HT agonists e.g. 1-(3-ethylbenzofuran-7-yl)piperazine oxalic acid salt (WO 01/09111), BR53 agonists, galanin antagonists, ghrelin antagonists, MCH antagonists, mGluR5 antagonists, opioid antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tert-butyl ester (WO 01/85695)), CNTF, CNTF derivatives (e.g. Axokine), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (e.g. bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is to be regarded as covered by the scope of protection of the present invention.

In two articles which appeared simultaneously in Nature (Nature 400, 261-264, 1999; Nature 400, 265-269, 1999), a highly specific receptor for melanine concentrating hormone (MCH) was described separately by two research groups. MCH assumes important functions in controlling food intake. Compounds acting on the MCH receptor therefore have an anorectic effect and are suitable for the treatment of obesity. Testing for an anorectic effect of the compounds of the invention of the formula I was therefore carried out as follows.

Functional Measurements to Find IC50 Values

The cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13 554-13 562, 2001). A difference from the reference was, however, the use of the plasmid pEAK8 from EDGE Biosystems (USA) to construct the expression vector. The host used for the transfection was a transformed HEK cell line named "PEAK Stable Cells" (likewise from EDGE Biosystems). The functional measurements of the cellular calcium flux after addition of agonist (MCH) in the presence of ligand of the invention took place with the aid of the FLIPR apparatus from Molecular Devices (USA) using the protocols of the apparatus manufacturer.

Biological Activity Testing

The IC50 values measured for exemplary compounds 33, 96 and 97 under the aforementioned conditions were of the order of from 0.01 to 10 μM.

General Explanations a) Mode of Drawing the Structural Formulae

Only non-H atoms are depicted for clarity in the structural formulae of the given examples. Carbon atoms are not written out as "C".

b) Salt Forms

Many of the compounds of the invention are bases and can form salts with appropriately strong acids. In particular, after purification of the compounds by HPLC chromatography using a trifluoroacetic acid-containing mobile phase they may be in the form of hydrotrifluoroacetates. These can be converted into the free bases shown by simple treatment of a solution of the salts for example with sodium carbonate solution.

c) Units of the Characterizing Data

The unit of the stated molecular weights is "g/mol". Peaks observed in the mass spectrum are indicated as integral quotient of the molar molecular ion mass and the charge of the molecular ion (m/z).

Abbreviations

Unless indicated otherwise, the abbreviations in the examples below have the following meaning:
NaBH₃CN=sodium cyanoborohydride
DMF=N,N-dimethylformamide
EDC=1-(3-dimethylaminopropyl)-3-ethylcarbodiimide
THF=tetrahydrofuran
DMSO=dimethyl sulfoxide
HOBt=1-hydroxybenzotriazole
HOAt=1-hydroxy-7-azabenzotriazole
HCl=hydrochloric acid
HPLC=high performance liquid chromatography
PyBOP=benzotriazol-1-yloxytris(pyrrolidino)phosphonium hexafluorophosphate
TOTU=O[(ethoxycarbonyl)cyanomethyleneamino]-N,N,N', N'-tetramethyluronium tetrafluoroborate
eq=equivalents

EXAMPLE 1

(1-{4-[5-(4-Butoxyphenyl)-[1,3,4]oxadiazol-2-yl]phenyl}pyrrolidin-3-yl)dimethylamine

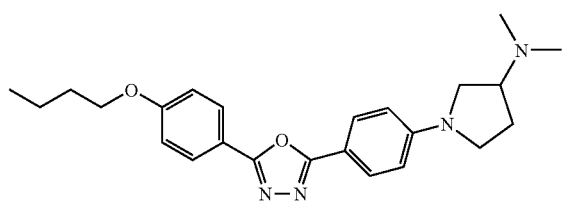

Method A

A mixture of 4-(3-dimethylaminopyrrolidin-1-yl)benzohydrazide (100 mg), 4-butoxy-benzoic acid (78 mg), 2-chloro-1,3-dimethyl-2-imidazolium hexafluorophosphate (112 mg), N,N-diisopropylethylamine (0.14 ml) and dichloromethane (5 ml) was stirred for 12 hours. Volatiles were removed, and the residue was purified by preparative HPLC. The product with the molecular weight of 406.53 (C24H30N4O2) was obtained in this way; MS (ESI): 407 (M+H+).

4-(3-Dimethylaminopyrrolidin-1-yl)benzohydrazide

A mixture of ethyl 4-(3-dimethylaminopyrrolidin-1-yl)benzoate (2.0 g), hydrazine hydrate (3.8 g) and ethanol (7 ml) was boiled under reflux for 15 hours. After cooling to 5° C., the resulting precipitate was filtered off with suction. The product with the molecular weight of 248.33 (C13H20N4O) was obtained in this way; MS (ESI): 249 (M+H+).

Ethyl 4-(3-dimethylaminopyrrolidin-1-yl)benzoate

A mixture of ethyl 4-fluorobenzoate (4.47 g), dimethylpyrrolidin-3-ylamine (3.04 g), potassium carbonate (3.68 g) and dimethyl sulfoxide (20 ml) was heated at 130° C. for 7 hours. After cooling, the mixture was diluted with water and extracted with methyl tert-butyl ether. The organic phase was washed with water, dried over magnesium sulfate, filtered and concentrated. The product with the molecular weight of 262.35 (C15H22N2O2) was obtained in this way; MS (ESI): 263 (M+H+).

EXAMPLE 2

Dimethyl-(1-{4-[5-(2-phenoxyethylsulfanylmethyl)-[1,3,4]oxadiazol-2-yl]phenyl}-pyrrolidin-3-yl)amine

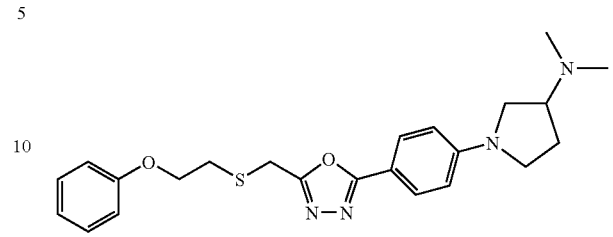

4-(3-Dimethylaminopyrrolidin-1-yl)benzohydrazide was reacted with (2-phenoxy-ethylsulfanyl)acetic acid by Method A. The product with the molecular weight of 424.57 (C23H28N4O2S) was obtained in this way; MS (ESI): 425 (M+H+).

EXAMPLE 3

Dimethyl-(1-{4-[5-(4-phenoxyphenyl)[1,3,4]oxadiazol-2-yl]phenyl}pyrrolidin-3-yl)amine

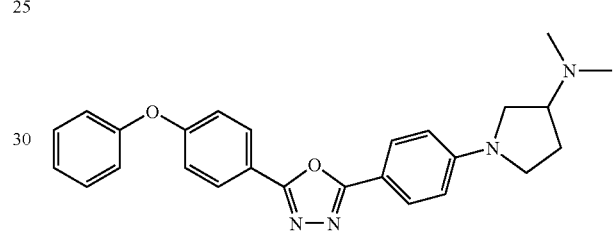

Method B

A mixture of N'-[4-(3-dimethylaminopyrrolidin-1-yl)benzoyl]-4-phenoxybenzohydrazide (178 mg), methoxycarbonylsulfamoyltriethylammonium hydroxide (Burgess' reagent) (96 mg) and 5 ml of toluene was stirred at 60° C. for 1 h. After the reaction was complete, the reaction mixture was filtered, and the filtrate was washed twice with ethyl acetate. The combined organic phases were subsequently washed with 5% strength sodium carbonate solution and then dried over Chromabond XTR. Volatiles were removed and the residue was purified by preparative HPLC. The product with the molecular weight of 426.21 (C26H26N4O2) was obtained in this way; MS (ESI): 427.21 (M+H+).

N'-[4-(3-Dimethylaminopyrrolidin-1-yl)benzoyl]4-phenoxybenzohydrazide

A mixture of 4-(3-dimethylaminopyrrolidin-1-yl)benzohydrazide (100 mg), 4-phenoxybenzoic acid (77.5 mg), 1-propanephosphonic anhydride 50% in dichloromethane (256 mg), N,N-diisopropylethylamine (0.208 ml) and DMF (3 ml) was stirred at room temperature for 72 h. The reaction mixture was then filtered, washed twice with ethyl acetate and shaken with 0.5N NaOH. Volatiles were removed and the residue was purified by preparative HPLC. The product with the molecular weight of 444.54 was obtained in this way; MS (ESI): 445.24 (M+H+).

4-(3-Dimethylaminopyrrolidin-1-yl)benzohydrazide was prepared as described in method A, with 1 eq of Burgess' reagent being added once again in some cases after heating for 1 h in the cyclization step, and then heating at 60° C. being continued for 1 hour.

Compounds 4-93 in table 1 were synthesized by method B.

| Ex. | Structure | Molecular formula | MW calc. | MW measured |
| --- | --- | --- | --- | --- |
| 4 | 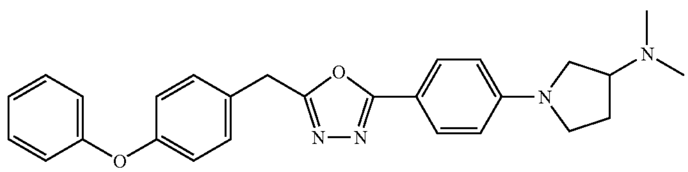 | C27H28N4O2 | 440.22 | 441.24 |
| 5 | 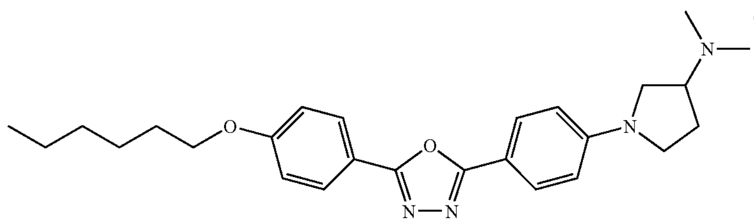 | C26H34N4O2 | 434.27 | 435.28 |
| 6 | 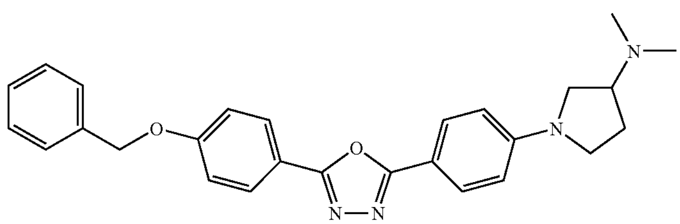 | C27H28N4O2 | 440.22 | 441.27 |
| 7 | 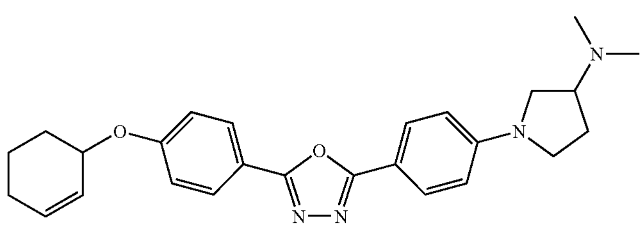 | C26H30N4O2 | 430.24 | 431.27 |
| 8 | 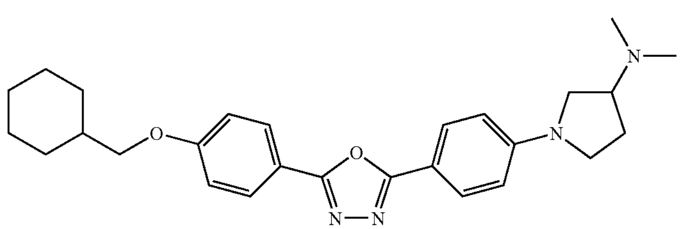 | C27H34N4O2 | 446.27 | 447.27 |
| 9 | 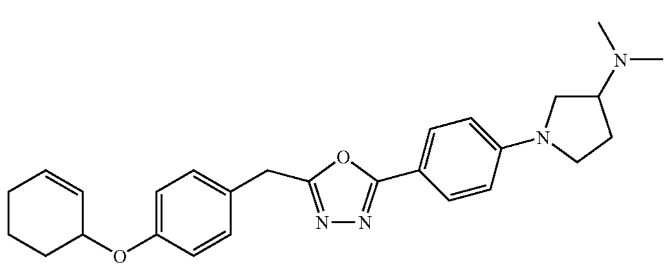 | C27H32N4O2 | 444.25 | 445.26 |

-continued
| Ex. | Structure | Molecular formula | MW calc. | MW measured |
|---|---|---|---|---|
| 10 | 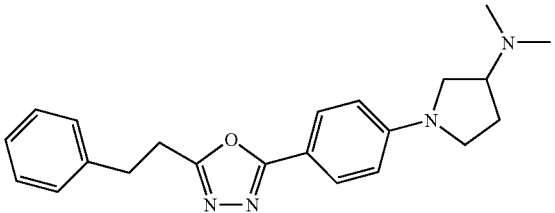 | C22H26N4O | 362.21 | 363.22 |
| 11 | 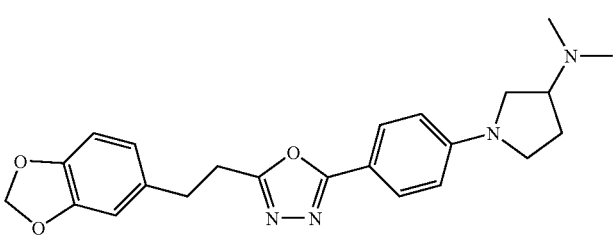 | C23H26N4O3 | 406.20 | 407.22 |
| 12 | 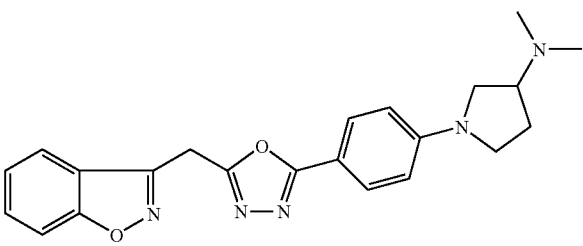 | C22H23N5O2 | 389.19 | 390.16 |
| 13 | 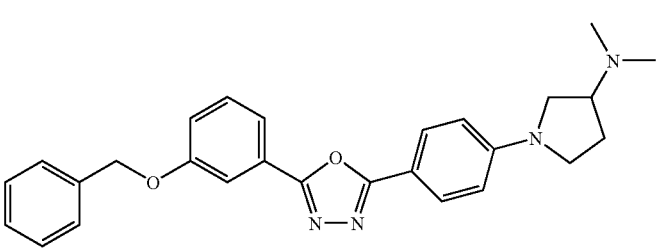 | C27H28N4O2 | 440.22 | 441.23 |
| 14 | 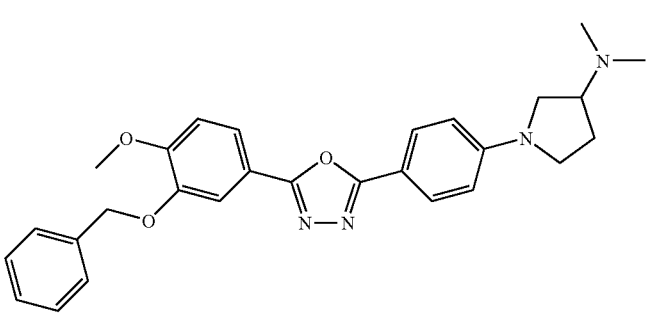 | C28H30N4O3 | 470.23 | 471.21 |
| 15 | 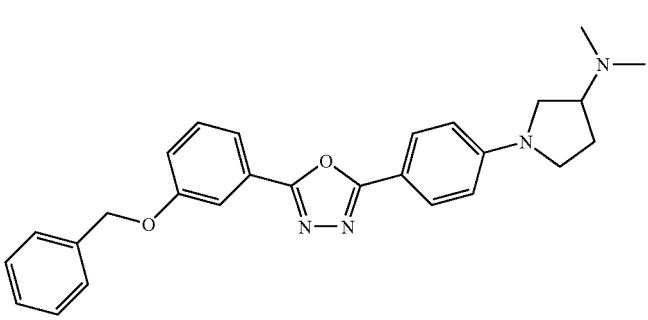 | C28H30N4O2 | 454.24 | 455.25 |

-continued

| Ex. | Structure | Molecular formula | MW calc. | MW measured |
|---|---|---|---|---|
| 16 | 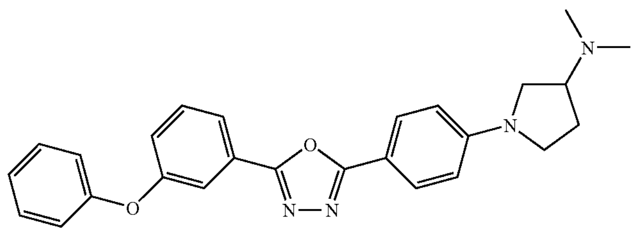 | C26H26N4O2 | 426.21 | 427.29 |
| 17 | 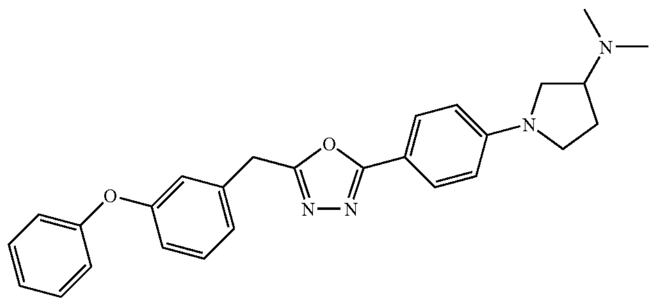 | C27H28N4O2 | 440.22 | 441.23 |
| 18 | 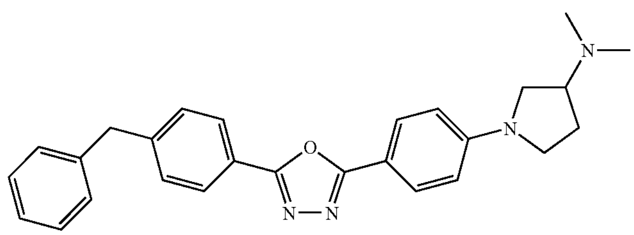 | C27H28N4O | 425.23 | 425.24 |
| 19 | 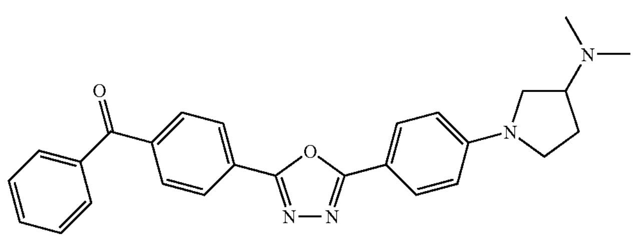 | C27H26N4O2 | 438.21 | 439.28 |
| 20 | 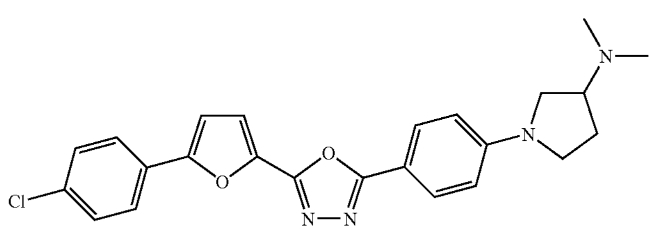 | C24H23ClN4O2 | 434.15 | 436.02 |
| 21 | 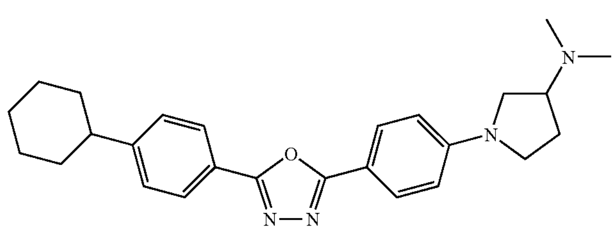 | C26H32N4O | 416.26 | 417.36 |

-continued

| Ex. | Structure | Molecular formula | MW calc. | MW measured |
|---|---|---|---|---|
| 22 | 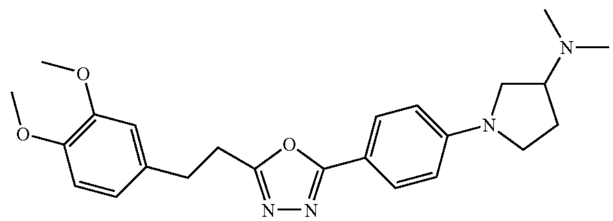 | C24H30N4O3 | 422.23 | 424.02 |
| 23 | 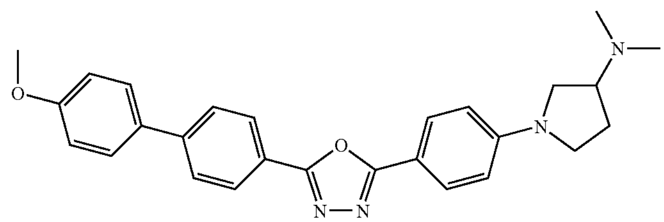 | C27H28N4O2 | 440.22 | 441.27 |
| 24 | 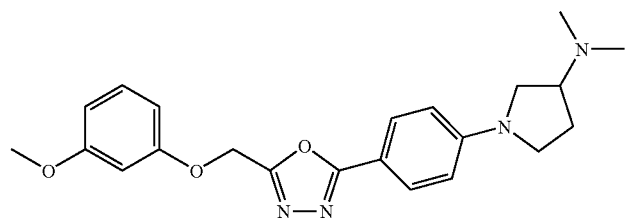 | C22H26N4O3 | 394.20 | 395.21 |
| 25 | 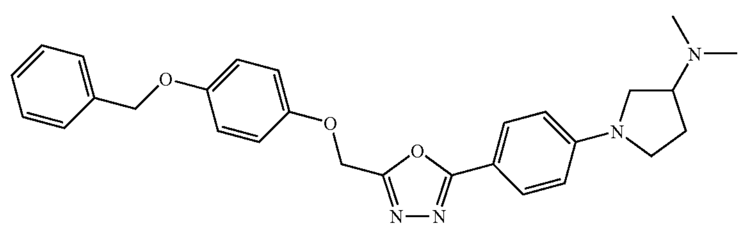 | C28H30N4O3 | 470.23 | 471.25 |
| 26 | 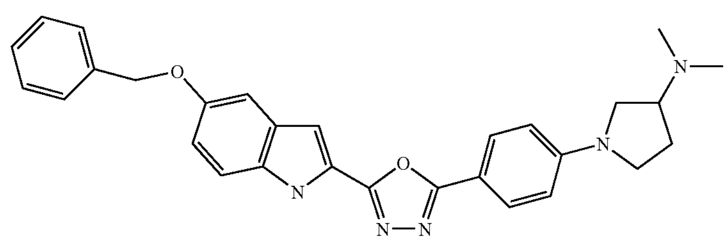 | C29H29N5O2 | 479.23 | 480.39 |
| 27 | 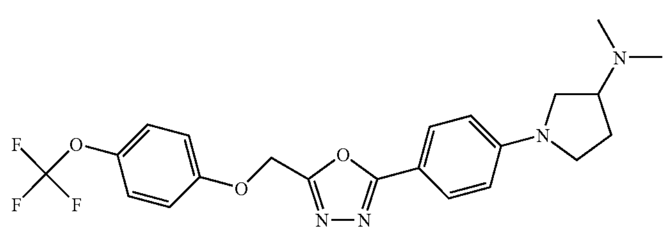 | C22H23F3N4O3 | 448.17 | 449.22 |

-continued

| Ex. | Structure | Molecular formula | MW calc. | MW measured |
|---|---|---|---|---|
| 28 | 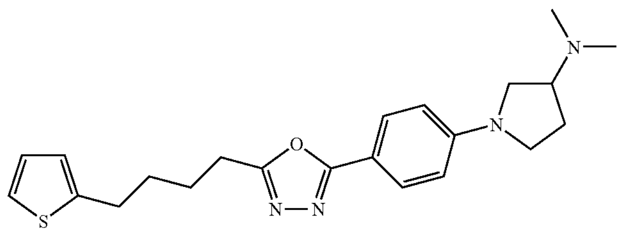 | C22H28N4OS | 396.20 | 397.22 |
| 29 | 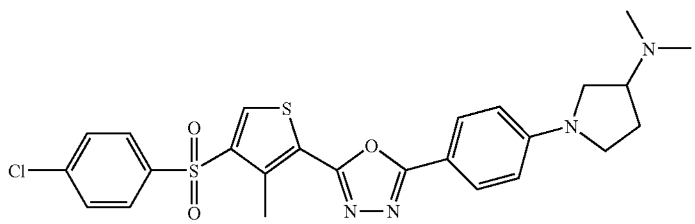 | C25H25ClN4O3S2 | 528.11 | 530.08 |
| 30 | 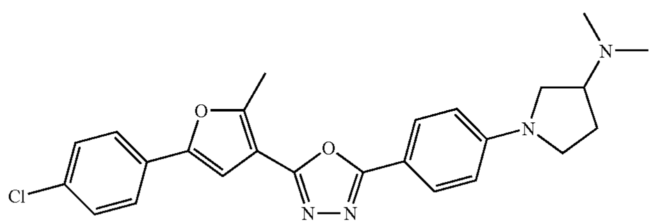 | C25H25ClN4O2 | 448.17 | 449.22 |
| 31 | 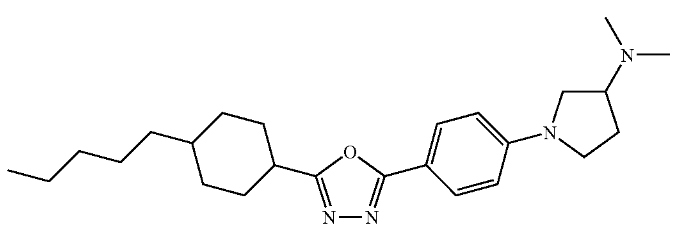 | C25H38N4O | 410.31 | 411.32 |
| 32 | 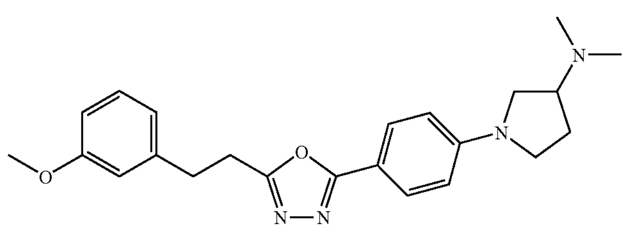 | C23H28N4O2 | 392.22 | 393.24 |
| 33 | 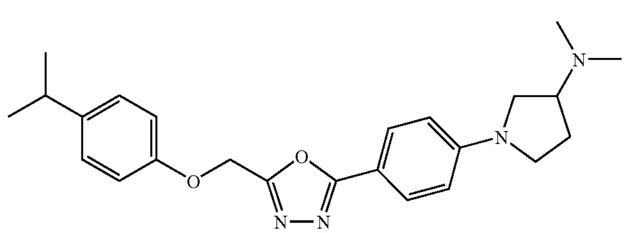 | C24H30N4O2 | 406.24 | 407.25 |

-continued

| Ex. | Structure | Molecular formula | MW calc. | MW measured |
|---|---|---|---|---|
| 34 | 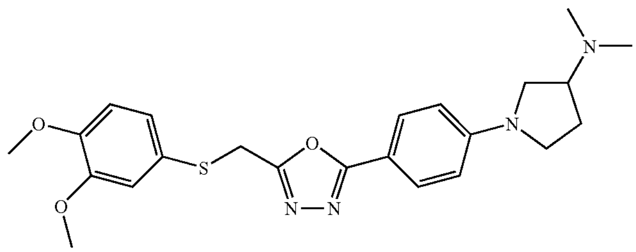 | C23H28N4O3S | 440.19 | 441.20 |
| 35 | 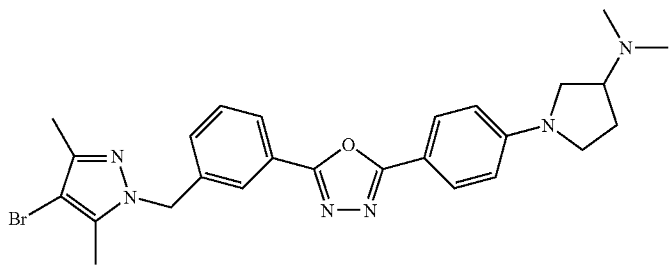 | C26H29BrN6O | 520.16 | 521.16 |
| 36 | 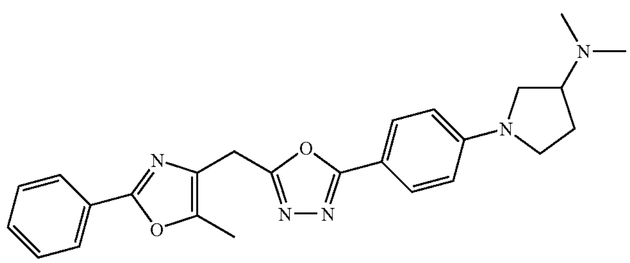 | C25H27N5O2 | 429.22 | 430.23 |
| 37 | 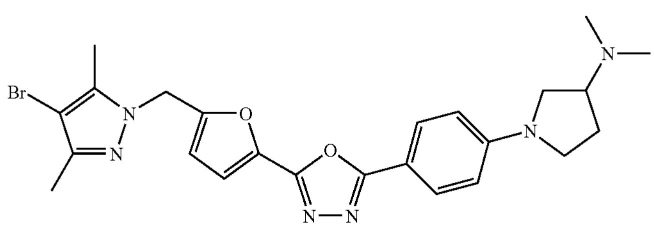 | C24H27BrN6O2 | 510.14 | 512.13 |
| 38 | 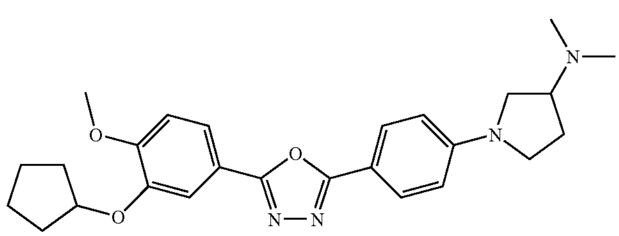 | C26H32N4O3 | 448.25 | 449.26 |
| 39 | 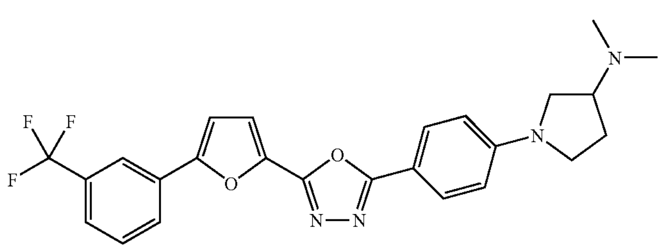 | C25H23F3N4O2 | 468.18 | 469.21 |

-continued

| Ex. | Structure | Molecular formula | MW calc. | MW measured |
|---|---|---|---|---|
| 40 | 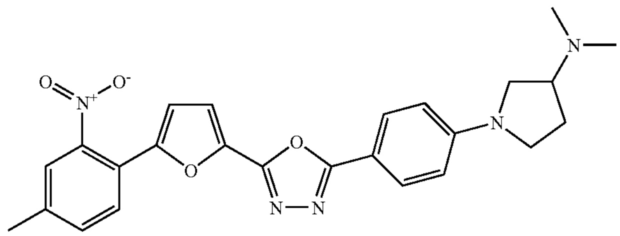 | C25H25N5O4 | 459.19 | 460.21 |
| 41 | 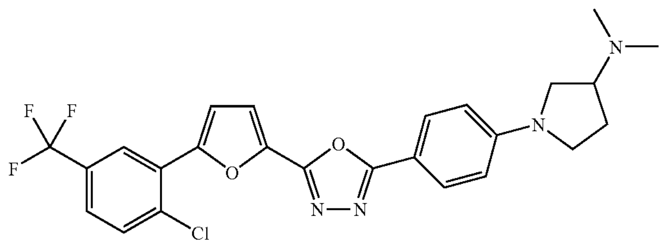 | C25H22ClF3N4O2 | 502.14 | 503.18 |
| 42 | 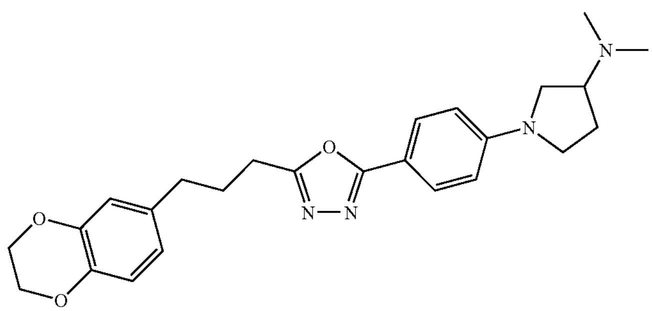 | C25H30N4O3 | 434.23 | 435.24 |
| 43 | 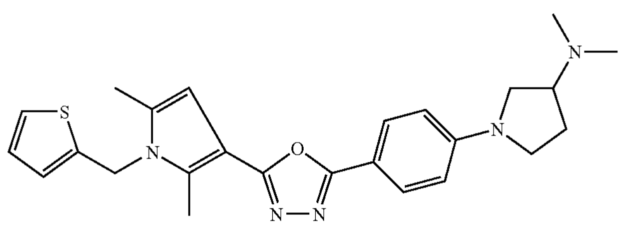 | C25H29N5OS | 447.21 | 448.21 |
| 44 | 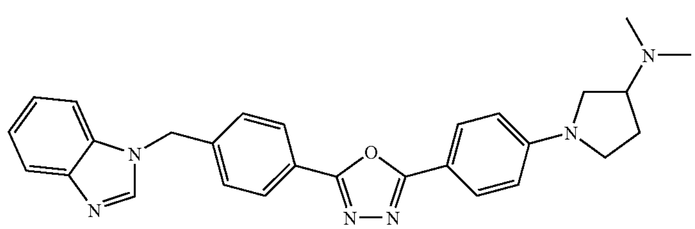 | C28H28N6O | 464.23 | 465.27 |
| 45 | 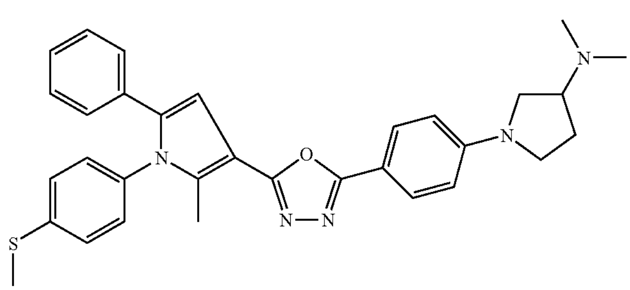 | C32H33N5OS | 535.24 | 536.25 |

US 7,319,108 B2

-continued

| Ex. | Structure | Molecular formula | MW calc. | MW measured |
|---|---|---|---|---|
| 46 | 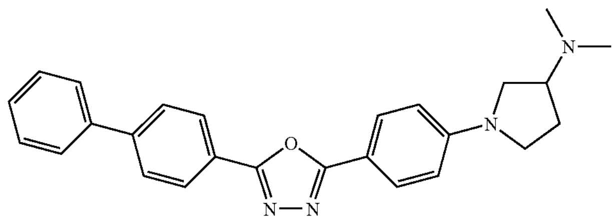 | C26H26N4O | 410.21 | 411.23 |
| 47 | 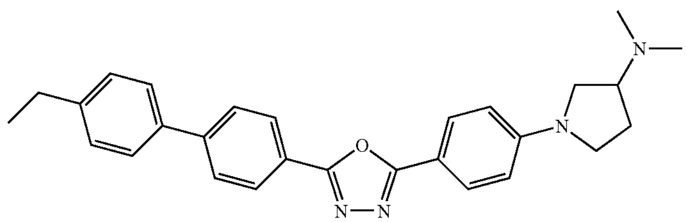 | C28H30N4O | 438.24 | 439.27 |
| 48 | 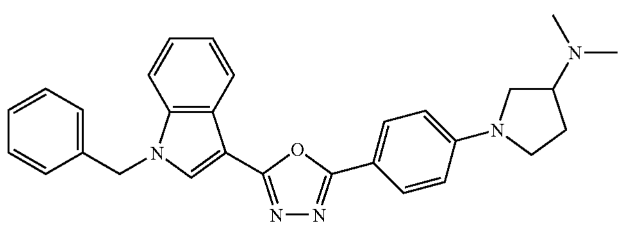 | C29H29N5O | 463.24 | 464.26 |
| 49 | 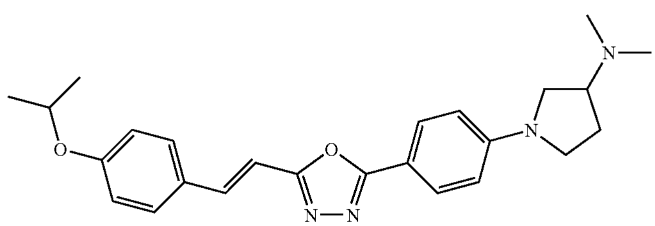 | C25H30N4O2 | 418.24 | 419.24 |
| 50 | 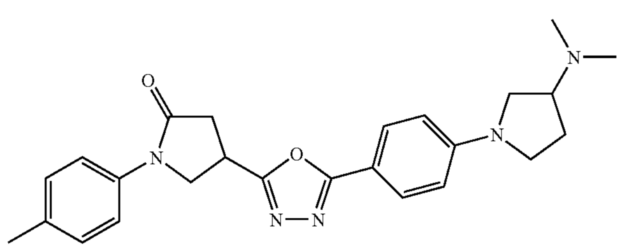 | C25H29N5O2 | 431.23 | 432.25 |
| 51 | 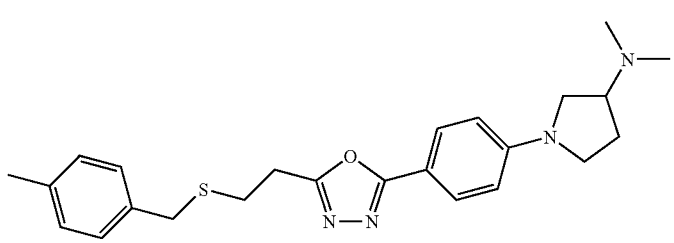 | C24H30N4OS | 422.21 | 423.23 |

-continued
| Ex. | Structure | Molecular formula | MW calc. | MW measured |
|---|---|---|---|---|
| 52 | 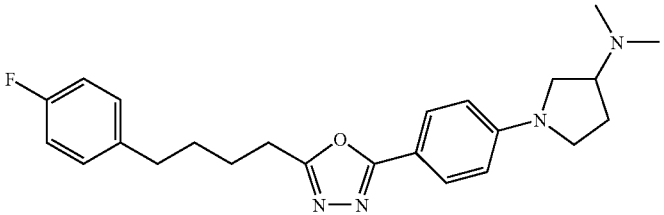 | C24H29FN4O | 408.23 | 409.24 |
| 53 | 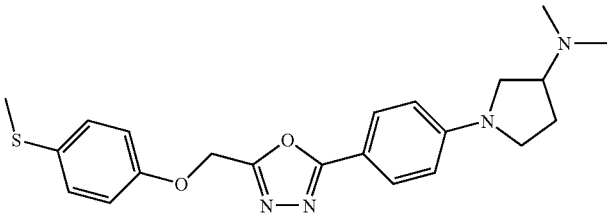 | C22H26N4O2S | 410.18 | 411.21 |
| 54 | 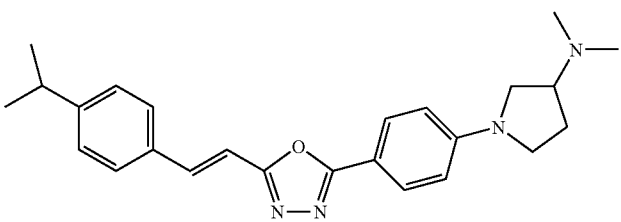 | C25H30N4O | 402.24 | 403.26 |
| 55 | 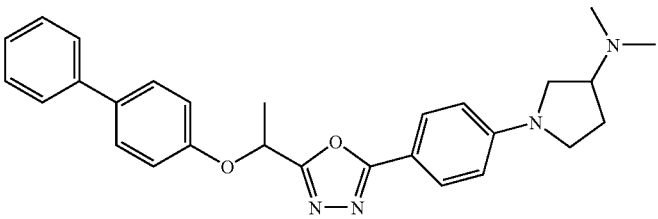 | C28H30N4O2 | 454.24 | 455.25 |
| 56 | 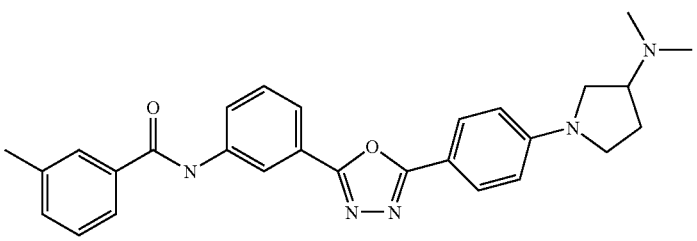 | C28H29N5O2 | 467.23 | 468.27 |
| 57 | 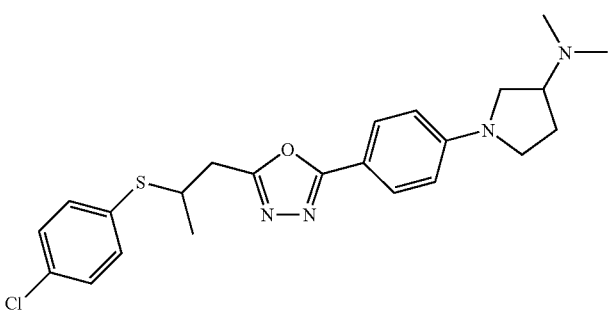 | C23H27ClN4OS | 442.16 | 443.17 |

-continued
| Ex. | Structure | Molecular formula | MW calc. | MW measured |
|---|---|---|---|---|
| 58 | 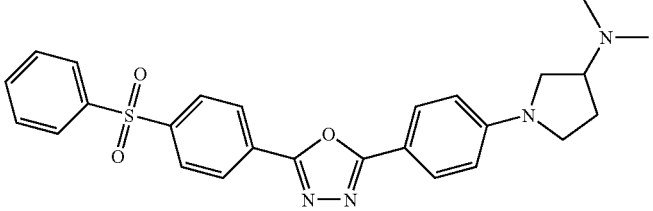 | C26H26N4O3S | 474.17 | 475.19 |
| 59 | 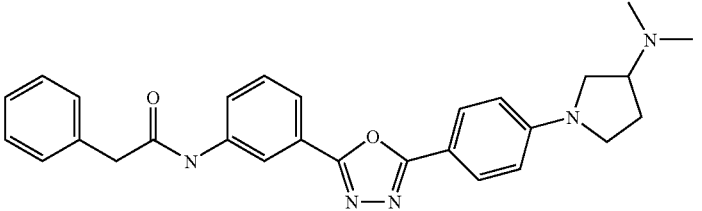 | C28H29N5O2 | 467.27 | 468.27 |
| 60 | 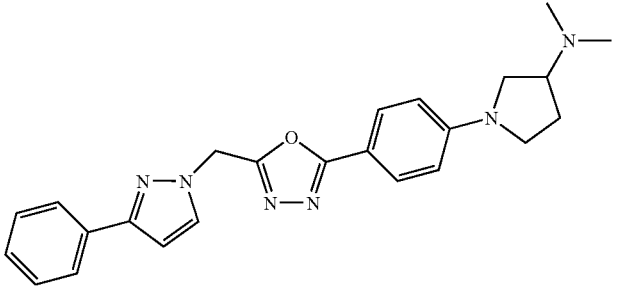 | C24H26N6O | 414.22 | 415.23 |
| 61 | 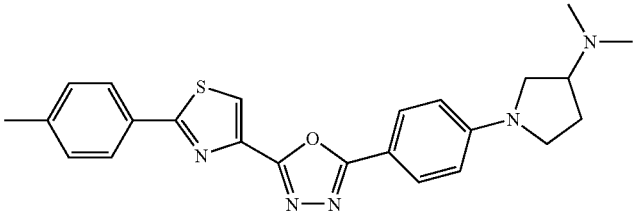 | C24H25N5OS | 431.18 | 432.19 |
| 62 | 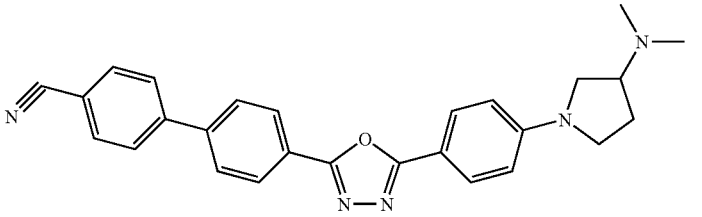 | C27H25N5O | 435.21 | 436.23 |
| 63 | 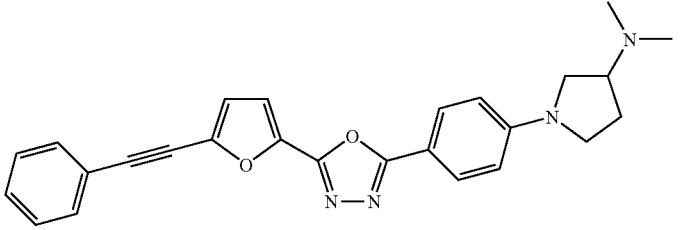 | C26H24N4O2 | 424.19 | 425.22 |

-continued
| Ex. | Structure | Molecular formula | MW calc. | MW measured |
|---|---|---|---|---|
| 64 | 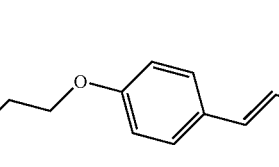 | C24H23FN4OS | 434.16 | 435.19 |
| 65 | 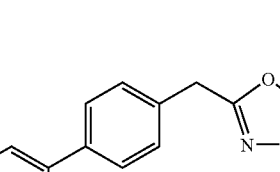 | C25H29FN4O2 | 436.23 | 437.26 |
| 66 | 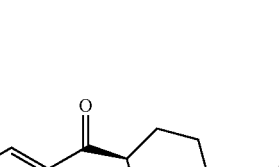 | C27H27FN4O | 442.22 | 443.24 |
| 67 | 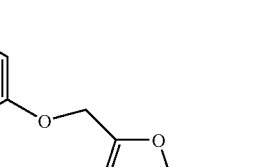 | C27H31FN4O2 | 462.24 | 464.36 |
| 68 | 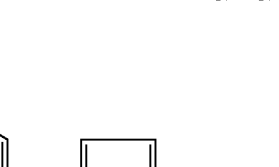 | C25H25ClN4O3 | 464.16 | 465.18 |
| 69 | 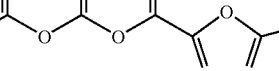 | C24H24N4O3 | 416.19 | 417.20 |

-continued
| Ex. | Structure | Molecular formula | MW calc. | MW measured |
|---|---|---|---|---|
| 70 | 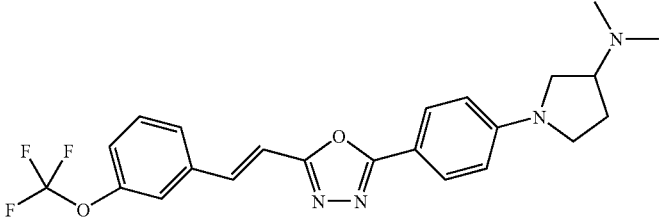 | C23H23F3N4O2 | 444.18 | 445.20 |
| 71 | 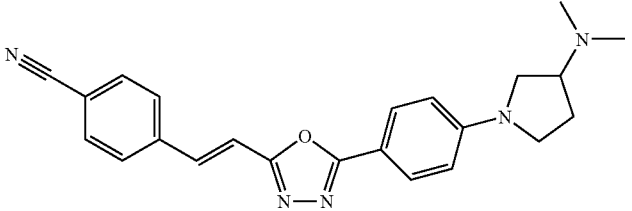 | C23H23N5O | 385.19 | 386.22 |
| 72 | Chiral 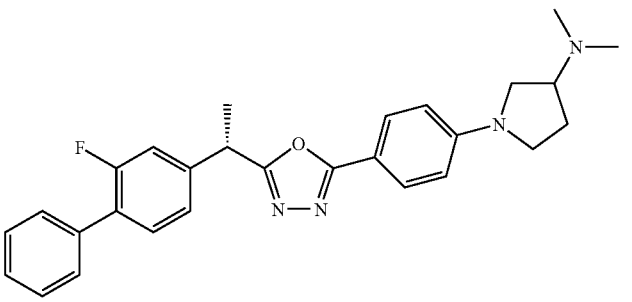 | C28H29FN4O | 456.23 | 457.25 |
| 73 | 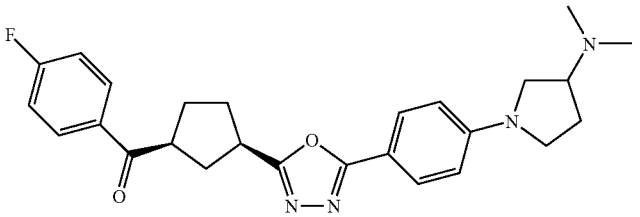 | C26H29FN4O2 | 448.23 | 449.24 |
| 74 | 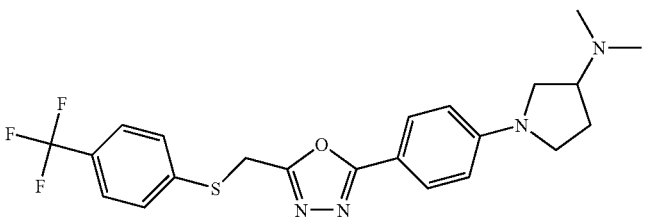 | C22H23F3N4OS | 448.15 | 449.16 |
| 75 | 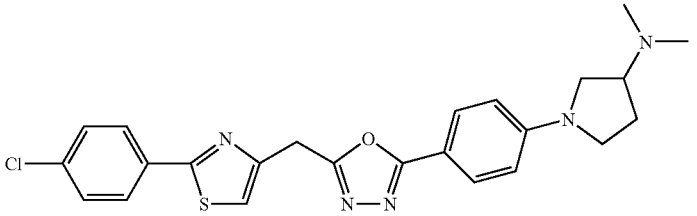 | C24H24ClN5OS | 465.14 | 466.15 |

-continued

| Ex. | Structure | Molecular formula | MW calc. | MW measured |
|---|---|---|---|---|
| 76 | 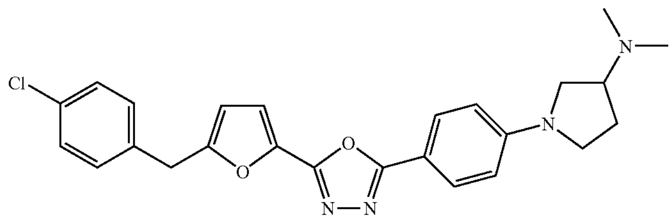 | C25H25ClN4O2 | 448.17 | 449.20 |
| 77 | 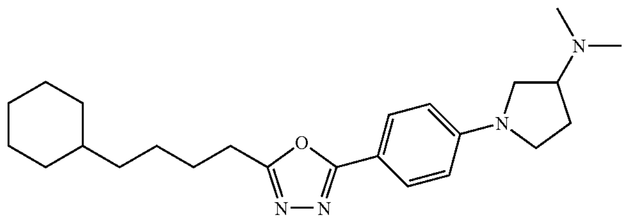 | C24H36N4O | 396.29 | 397.31 |
| 78 | 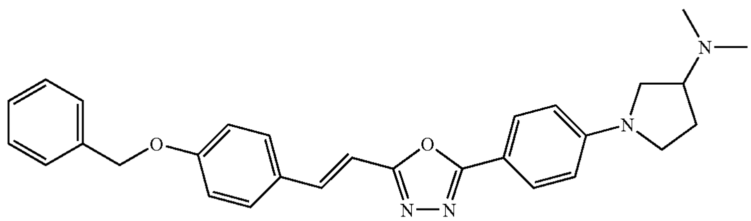 | C29H30N4O2 | 466.24 | 467.27 |
| 79 | 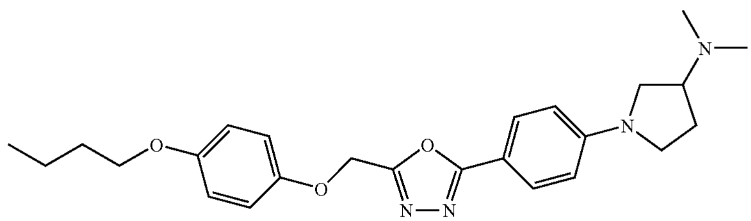 | C25H32N4O3 | 436.25 | 437.27 |
| 80 | 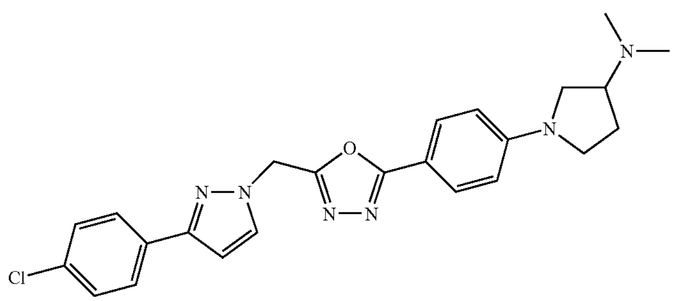 | C24H25ClN6O | 448.18 | 449.21 |
| 81 | 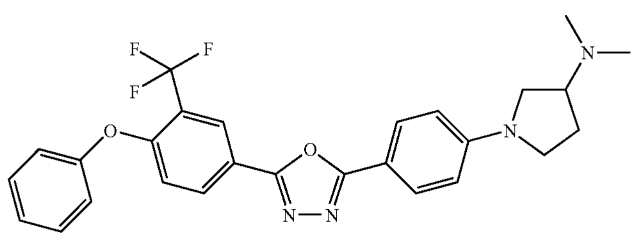 | C27H25F3N4O2 | 494.19 | 495.22 |

-continued

| Ex. | Structure | Molecular formula | MW calc. | MW measured |
|---|---|---|---|---|
| 82 | 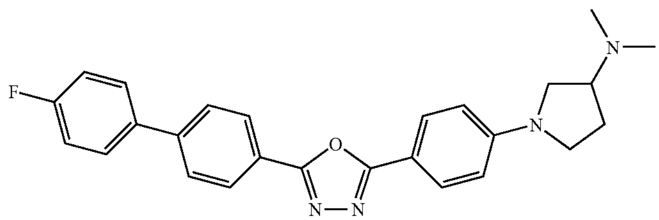 | C26H25FN4O | 428.20 | 429.23 |
| 83 | 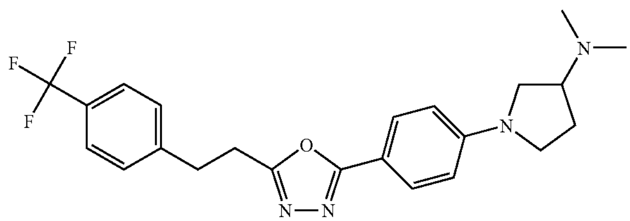 | C23H25F3N4O | 430.20 | 431.20 |
| 84 | 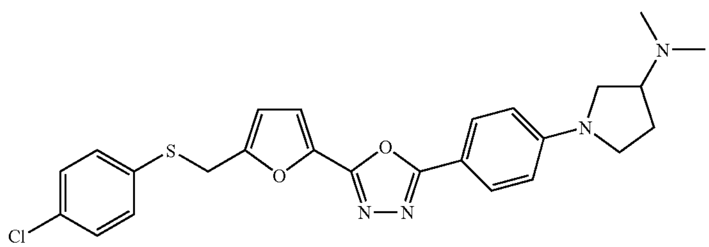 | C25H25ClN4O2S | 480.14 | 481.17 |
| 85 | 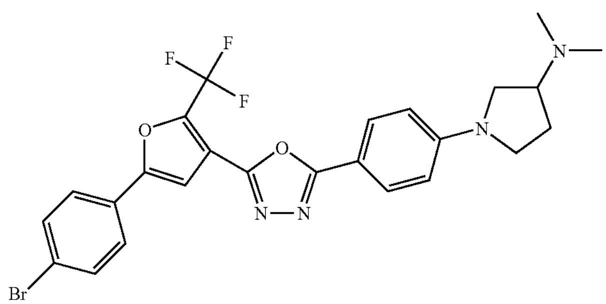 | C25H22BrF3N4O2 | 546.09 | 547.11 |
| 86 | 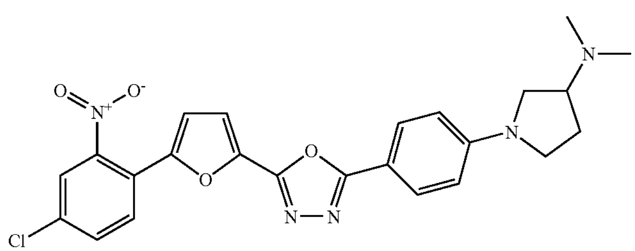 | C24H22ClN5O4 | 479.14 | 480.15 |
| 87 | 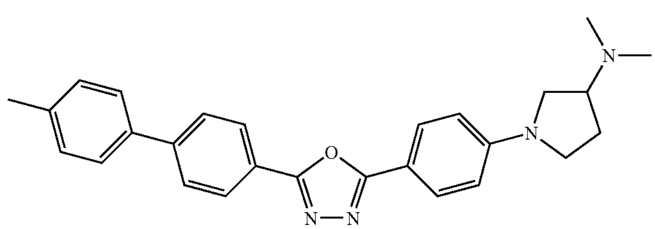 | C27H28N4O | 424.23 | 425.24 |

-continued

| Ex. | Structure | Molecular formula | MW calc. | MW measured |
|---|---|---|---|---|
| 88 | 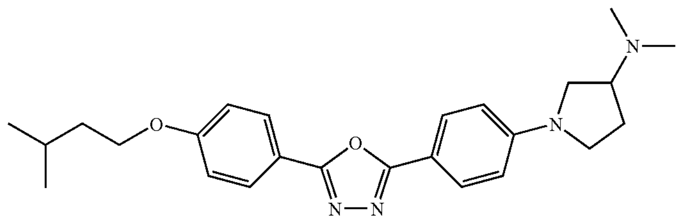 | C25H32N4O2 | 420.25 | 421.26 |
| 89 | 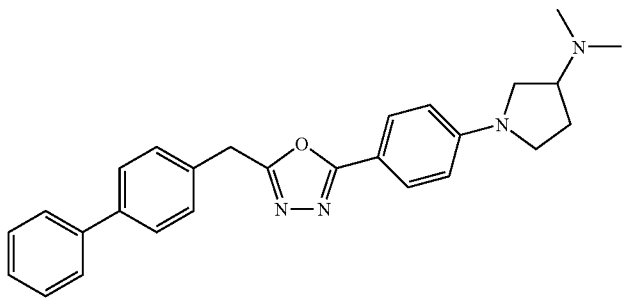 | C27H28N4O | 424.23 | 425.24 |
| 90 | 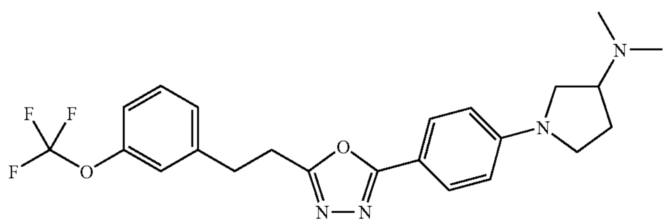 | C23H25F3N4O2 | 446.19 | 447.19 |
| 91 | 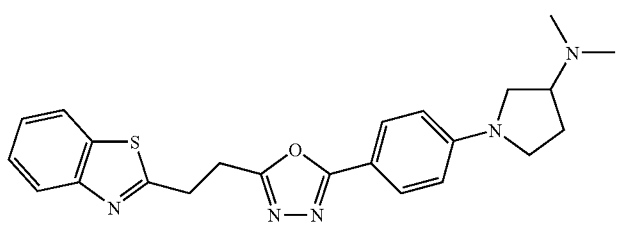 | C23H25N5OS | 419.18 | 420.11 |
| 92 | 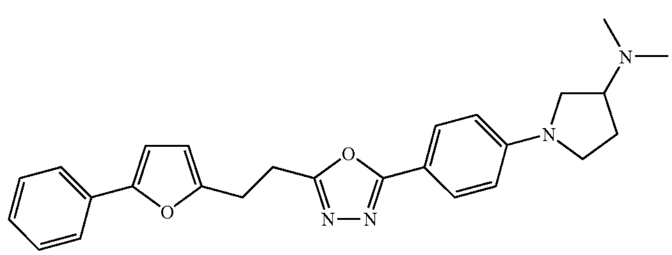 | C26H28N4O2 | 428.22 | 429.24 |

EXAMPLE 93

Dimethyl-(1-{4-[5-(4-phenoxybutyl)[1,3,4]oxadiazol-2-yl]phenyl}pyrrolidin-3-yl)amine

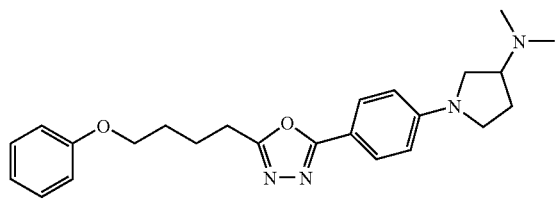

PyBOP (25.2 mg) was added to a mixture of 4-phenoxybutanohydrazide (10 mg), 4-(3-dimethylaminopyrrolidin-1-yl)benzoic acid (12.1 mg), HOAt (6.6 mg), triethylamine (13.5 μl) and DMF (0.15 ml) at 0° C. The mixture was stirred at 0° C. for 10 min and then at room temperature for 3 h. Ethyl acetate and water were then added to the reaction solution. The organic phase was subsequently washed twice each with 10% strength citric acid solution, saturated sodium bicarbonate solution and water and dried over sodium sulfate, and the solvent was removed in vacuo.

The residue was then taken up in THF (0.4 ml), and EDC (6.1 mg) and triethylamine (5.5 μl) were added, and the mixture was stirred at 50° C. for 16 h. Ethyl acetate and water were then added to the reaction solution. The organic phase subsequently washed twice each with 10% strength citric acid solution, saturated sodium bicarbonate solution and water and dried over sodium sulfate, and the solvent removed in vacuo. The residue was purified by preparative HPLC. The product with the molecular weight of 406.53 (C24H30N4O2) was obtained in this way; MS (ESI): 407.15 (M+H+).

4-Phenoxybutanohydrazide

A mixture of phenol (100 mg), ethyl 5-bromovalerate (222.2 mg), cesium carbonate (693 mg) and DMF (1.6 ml) was stirred at room temperature for 12 h. Ethyl acetate and water were then added to the reaction solution, and the aqueous phase was adjusted to pH 6 with 2N HCl solution. The aqueous phase extracted twice more with ethyl acetate. The combined organic phases were then washed with water and dried over sodium sulfate, and the solvent was removed in vacuo. The product obtained in this way was taken up in abs. ethanol (0.5 ml), 37.3 μl of hydrazine hydrate were added, and the mixture was heated under reflux for 12 h. Ethyl acetate and water were then added to the reaction solution, and the aqueous phase was neutralized with 2N HCl solution. The aqueous phase was extracted twice with ethyl acetate. The combined organic phases were then washed with water and dried over sodium sulfate, and the solvent was removed in vacuo. The residue was purified by preparative HPLC. The product with the molecular weight of 208.11 (C11H16ClN2O2) was obtained in this way; MS (ESI): 209.1 (M+H+).

4-(3-Dimethylaminopyrrolidin-1-yl)benzoic Acid

A 1M sodium cyanoborohydride solution (1.32 ml) was added to a mixture of methyl 4-(3-aminopyrrolidin-1-yl)benzoate (300 mg), acetic acid (81 μl), formaldehyde (0.113 ml) and THF (3 ml). The reaction was stirred at room temperature for 1 h, then the solvent was removed in vacuo, and the residue was taken up again in ethyl acetate/water. The organic phase was washed with water and dried over sodium sulfate, and the solvent was removed in vacuo.

The product obtained in this way was dissolved in a THF/water mixture (1:1) (3.1 ml), and potassium hydroxide (66.2 mg) was added. The reaction was heated at 70° C. for 4 h. Ethyl acetate and water were then added to the reaction solution, and the aqueous phase was acidified with 2N HCl solution. The aqueous phase was extracted twice with ethyl acetate. The combined organic phases were then washed with water and dried over sodium sulfate, and the solvent was removed in vacuo. The product with the molecular weight of 234.17 (C13H18N2O2) was obtained in this way; MS (ESI): 235.10 (M+H+).

Methyl 4-(3-aminopyrrolidin-1-yl)benzoate

A mixture of 3-(tert-butoxycarbonylamino)pyrrolidine (1 g), methyl 4-fluorobenzoate (0.83 ml), cesium carbonate (1.7 g) and DMF (10 ml) was heated at 100° C. for 12 h. Ethyl acetate and water were then added to the reaction solution. The organic phase was then washed twice with water and dried over sodium sulfate, and the solvent was removed in vacuo.

The product obtained in this way was dissolved in methylene chloride (12 ml), trifluoroacetic acid (6 ml) was added, and the mixture was stirred at room temperature for 90 min. The solvent was removed in vacuo, and the residue was purified by preparative HPLC. The product with the molecular weight of 220.12 (C12H16N2O2) was obtained in this way; MS (ESI): 221.10 (M+H+).

EXAMPLE 94

(1-{4-[5-(4-Butoxyphenyl)-[1,3,4]thiadiazol-2-yl]phenyl}pyrrolidin-3-yl)dimethylamine

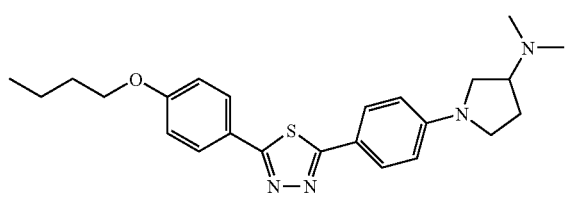

A mixture of N'-(4-butoxybenzoyl)-4-(3-dimethylaminopyrrolidin-1-yl)benzohydrazide (100 mg), Lawesson's reagent (191 mg) and toluene (5 ml) was boiled under reflux for 4 hours. Volatiles were removed, and the residue was purified by preparative HPLC. The product with the molecular weight of 422.60 (C24H30N4OS) was obtained in this way; MS (ESI): 423 (M+H+).

N'-(4-Butoxybenzoyl)-4-(3-dimethylaminopyrrolidin-1-yl)benzohydrazide

A mixture of 4-butoxybenzoic acid (156 mg) and DMF (10 ml) was mixed with TOTU (264 mg) and N,N-diisopropylethylamine (104 mg). After 10 minutes, 4-(3-dimethylaminopyrrolidin-1-yl)benzohydrazide (200 mg) was added. After one hour, the mixture was diluted with water and extracted with ethyl acetate. The organic phase was washed with water, dried over magnesium sulfate, filtered

EXAMPLE 95

((R)-3-{4-[5-(4-Chlorophenoxymethyl)[1,2,4]oxadiazol-3-yl]phenyl}cyclopentyl)-methylamine

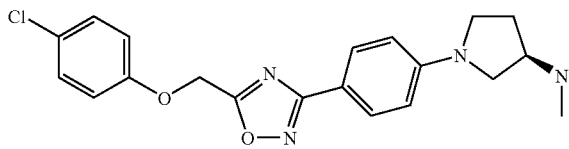

PyBOP (558 mg), HOAt (146 mg) and triethylamine (0.299 ml) were added to a mixture of tert-butyl {(R)-1-[4-(N-hydroxycarbamimidoyl)phenyl]pyrrolidin-3-yl}methylcarbamate (358.5 mg), (4-chlorophenoxy)acetic acid (200 mg) and 3 ml of DMF at 0° C., and the reaction mixture was stirred at this temperature for 10 min. It was then stirred at room temperature for 2 h and ethyl acetate and water were added to the reaction solution. The organic phase was then washed twice each with 10% strength citric acid solution, saturated sodium bicarbonate solution and water, dried over sodium sulfate and filtered, and the solvent was removed in vacuo.

The residue was then taken up in 10 ml of THF, and EDC (160 mg) and triethylamine (0.144 ml) were added, and the mixture was stirred at 50° C. for 16 h. Ethyl acetate and water were then added to the reaction solution. The organic phase was then washed twice each with 10% strength citric acid solution, saturated sodium bicarbonate solution and water, dried over sodium sulfate and filtered, and the solvent was removed in vacuo.

The crude product was taken up in methylene chloride (7.2 ml), and trifluoroacetic acid (1.8 ml) was added. The reaction was stirred at room temperature for 5 h and then the solvent was removed in vacuo. The residue was purified by preparative HPLC. The product with the molecular weight of 384.14 (C20H21ClN4O2) was obtained in this way; MS(ESI): 385.26 (M+H+).

(4-Chlorophenoxy)acetic Acid

A mixture of 4-chlorophenol (500 mg), methyl bromoacetate (0.368 ml), cesium carbonate (1.9 g) and 5 ml of acetone was stirred at room temperature for 12 h. Ethyl acetate and water were then added to the reaction solution, and the organic phase was washed twice with water, dried over sodium sulfate and filtered, and the solvent was removed in vacuo. The crude product was dissolved in a 1:1 THF/water mixture (10 ml), and potassium hydroxide (417 mg) was added. The reaction was stirred at room temperature for 12 h. Ethyl acetate and water were then added to the reaction solution, and the aqueous phase was adjusted to pH 2 and extracted several times with ethyl acetate. The combined organic phases were washed twice with water, dried over sodium sulfate and filtered, and the solvent was removed in vacuo. The product with the molecular weight of 186.6 (C8H7ClO3) was obtained in this way; MS (ESI): 227.0 (M+CH3CN).

{(R)-1-[4-(N-Hydroxycarbamimidoyl)phenyl]pyrrolidin-3-yl}methylcarbamic Acid Tert-Butyl Ester Sodium hydride (253.4 mg) was added in portions to a solution of tert-butyl [(R)-1-(4-cyanophenyl)pyrrolidin-3-yl]carbamate (1.06 g) in 12 ml of DMF at 0° C. After removal of the ice bath, methyl iodide (0.498 ml) was added dropwise to the reaction solution, which was stirred at room temperature for 4 h. Ethyl acetate and water were then added to the reaction solution, and the organic phase was washed twice with water, dried over sodium sulfate and filtered, and the solvent was removed in vacuo.

The crude product was dissolved in abs. ethanol (12 ml), and hydroxylamine (0.687 ml) was added. The reaction solution was heated under reflux for 12 h. Ethyl acetate and water were then added to the reaction solution, and the organic phase was washed twice with water and dried over sodium sulfate, and the solvent was removed in vacuo. The residue was purified by preparative HPLC. The product with the molecular weight of 334.42 (C17H26N4O3) was obtained in this way; MS (ESI): 335.20 (M+H+).

[(R)-1-(4-Cyanophenyl)pyrrolidin-3-yl]carbamic Acid

A mixture of (3R)-(+)-(tert-butoxycarbonylaminopyrrolidine (1.0 g), p-fluorobenzonitrile (650 mg), cesium carbonate (1.75 g) and 5 ml of DMF was stirred at 50° C. for 12 h. Ethyl acetate and water were then added to the reaction solution, and the organic phase was washed twice with water, dried over sodium sulfate and filtered, and the solvent was removed in vacuo. The residue was purified by preparative HPLC. The product with the molecular weight of 287.36 (C16H21N3O2) was obtained in this way; MS (ESI): 288.20 (M+H+).

EXAMPLE 96

((R)-1-{4-[5-(4-Chlorobenzyloxymethyl)[1,2,4]oxadiazol-3-yl]phenyl}pyrrolidin-3-yl)methylamine

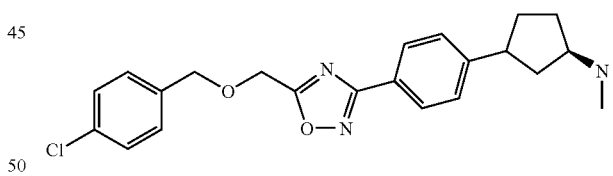

A solution of (4-chlorobenzyloxy)acetic acid (70 mg) in thionyl chloride (1 ml) was stirred at room temperature for 1 h, and then toluene was added and the solvent was stripped off in vacuo. This procedure was repeated twice more. The acid chloride was then taken up in methylene chloride (1.4 ml), {(R)-1-[4-(N-hydroxycarbamimidoyl)phenyl]pyrrolidin-3-yl}methylcarbamic acid tert-butyl ester (116.7 mg), triethylamine (0.05 ml) were added, and the mixture was stirred at room temperature for 12 h. The volatile components were removed in vacuo, and the residue was taken up in ethyl acetate/water. The organic phase was washed twice with water and dried over sodium sulfate, and the solvent was removed in vacuo. The residue was purified by preparative HPLC. The product with the molecular weight of 398.15 (C21H23ClN4O2) was obtained in this way; MS (ESI): 399.41 (M+H+).

(4-Chlorobenzyloxy)acetic acid was prepared in analogy to (4-chlorophenoxy)-acetic acid using 4-chlorobenzyl bromide as precursor. The product with the molecular weight of 200.62 (C9H9ClO3) was obtained in this way; MS (ESI): 222.95 (M+Na—H).

EXAMPLE 97

4-Chloro-N-{3-[4-(3-dimethylaminopyrrolidin-1-yl)phenyl][1,2,4]oxadiazol-5-ylmethyl}benzamide

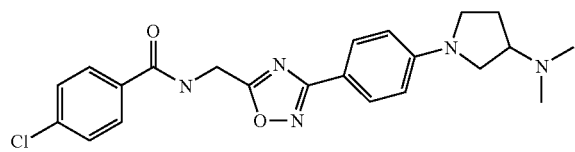

Method C

TOTU (51.4 mg) and N,N-diisopropylethylamine (0.05 ml) were added to a mixture of {1-[4-(5-aminomethyl[1,2,4]oxadiazol-3-yl)phenyl]pyrrolidin-3-yl}dimethylamine (75.3 mg), 4-chlorobenzoic acid (23.5 mg) and DMF (0.96 ml), and the solution was stirred at room temperature for 12 h. The crude product was purified by preparative HPLC (RP) and then purified again by chromatography on silica gel (dichloromethane/MeOH/AcOH/H$_2$O=90/10/1/1). The product with the molecular weight of 425.16 (C22H24ClN5O2) was obtained in this way; MS (ESI): 426.17 (M+H).

{1-[4-(5-Aminomethyl[1,2,4]oxadiazol-3-yl)phenyl]pyrrolidin-3-yl}dimethylamine

PyBOP (546.4 mg), HOAt (136.1 mg) and triethylamine (0.279 ml) were added to a mixture of 4-(3-dimethylaminopyrrolidin-1-yl)-N-hydroxybenzamidine (248.3 mg), tert-butoxycarbonylaminoacetic acid (175.2 mg) and DMF (2.8 ml) at 0° C. and the mixture was stirred at this temperature for 10 min. It was subsequently stirred at room temperature for 2 h and then ethyl acetate and water were added to the reaction solution. The organic phase then washed twice each with 10% strength citric acid solution, saturated sodium bicarbonate solution and water, dried over sodium sulfate and filtered, and the solvent removed in vacuo. The residue was then taken up in 6.2 ml of THF, and EDC (105 mg) and triethylamine (0.09 ml) were added, and the mixture was stirred at 50° C. for 16 h. Ethyl acetate and water were then added to the reaction solution. The organic phase then washed twice each with 10% strength citric acid solution, saturated sodium bicarbonate solution and water and dried over sodium sulfate, and the solvent removed in vacuo. The crude product was taken up in methylene chloride (9.6 ml), and trifluoroacetic acid (2.3 ml) was added. The reaction was stirred at room temperature for 5 h and then the solvent was removed in vacuo. The residue was purified by preparative HPLC. The product with the molecular weight of 287.37 (C$_{15}$H$_{21}$N$_{5}$O) was obtained in this way; MS (ESI): 288.05 (M+H+).

4-(3-Dimethylaminopyrrolidin-1-yl)-N-hydroxybenzamidine

A mixture of 3-(dimethylamino)pyrrolidine (1.1 g), p-fluorobenzonitrile (1.2 g), potassium carbonate (2.8 g) and acetonitrile (15 ml) was stirred at 80° C. for 12 h. The reaction solution was then filtered, and the precipitate was washed with acetonitrile, the solvent was removed in vacuo, and the residue was taken up again in ethyl acetate. The ethyl acetate phase was washed twice with water and then dried over sodium sulfate, and the solvent was removed in vacuo. The product obtained in this way was dissolved in abs. ethanol (48.7 ml), and hydroxylamine (1.4 ml) was added to the solution. The reaction mixture was heated under reflux for 12 h. The precipitate obtained after cooling the reaction solution was filtered off and washed with a little ethanol.

The product with the molecular weight of 248.33 (C13H20N4O) was obtained in this way; MS (ESI): 249.15 (M+H+).

Examples 98-110 in table 2 were synthesized by method C.

| Ex. | Structure | Molecular formula | MW calc. | MW measured |
|---|---|---|---|---|
| 98 | 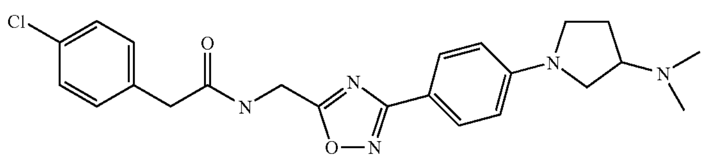 | C23H26ClN5O2 | 439.18 | 440.19 |
| 99 | 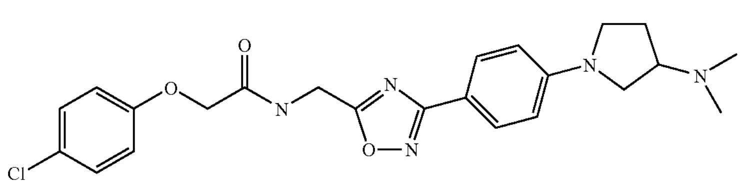 | C23H26ClN5O3 | 455.17 | 456.17 |

-continued

| Ex. | Structure | Molecular formula | MW calc. | MW measured |
|---|---|---|---|---|
| 100 | 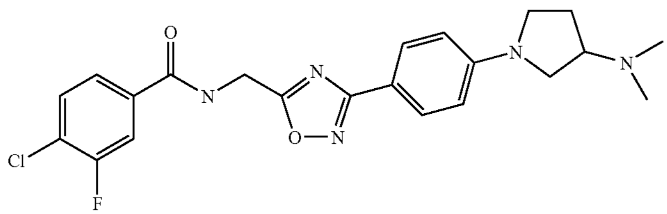 | C22H23ClFN5O2 | 443,15 | 444.21 |
| 101 | 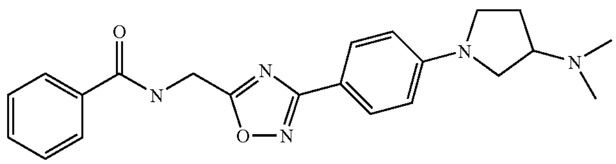 | C22H25N5O2 | 391.20 | 392.25 |
| 102 | 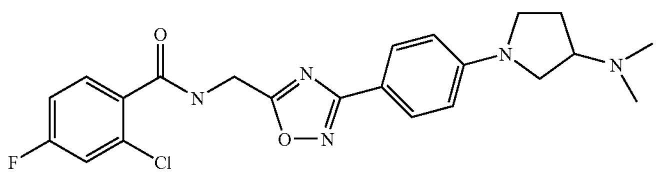 | C22H23ClFN5O2 | 443.15 | 444.21 |
| 103 | 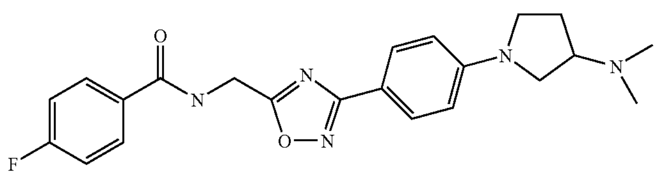 | C22H24FN5O2 | 409.19 | 410.22 |
| 104 | 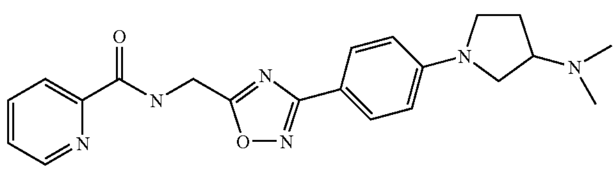 | C21H24N6O2 | 392.20 | 393.24 |
| 105 | 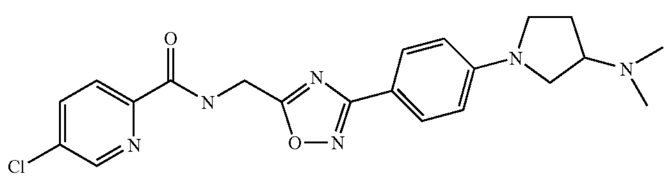 | C21H23ClN6O2 | 426.16 | 427.19 |
| 106 | 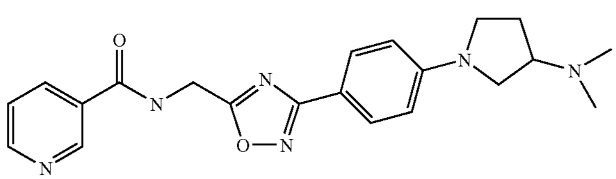 | C21H24N6O2 | 392.20 | 393.25 |
| 107 | 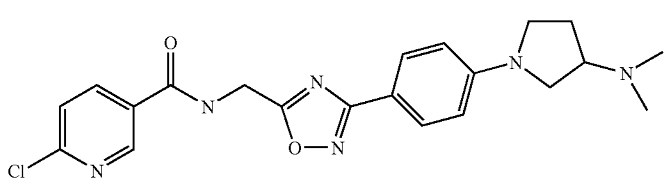 | C21H23ClN6O2 | 426.16 | 427.20 |

-continued

| Ex. | Structure | Molecular formula | MW calc. | MW measured |
|---|---|---|---|---|
| 108 | 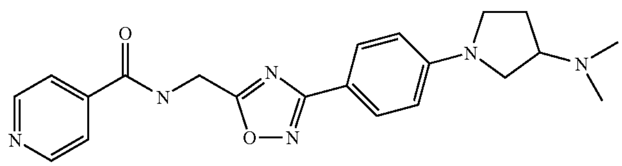 | C21H24N6O2 | 392.20 | 393.26 |
| 109 | 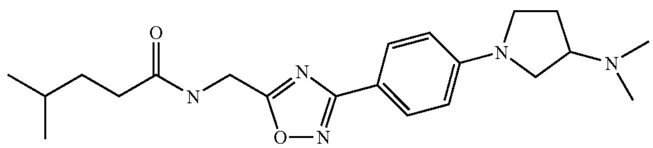 | C21H31N5O2 | 385.25 | 386.27 |
| 110 | 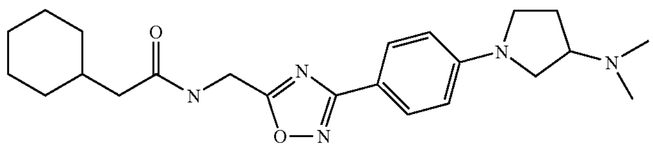 | C23H33N5O2 | 411.26 | 412.30 |

EXAMPLE 111

[1-(4-{5-[(4-Chlorobenzylamino)methyl][1,2,4]oxadiazol-3-yl}phenyl)pyrrolidin-3-yl]-dimethylamine

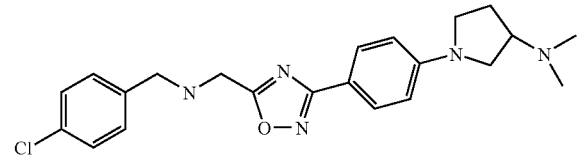

Method D

Polymer-bound sodium cyanoborohydride (5 eq) was added to a mixture of {1-[4-(5-aminomethyl[1,2,4]oxadiazol-3-yl)phenyl]dimethylamine (40.1 mg), 4-chlorobenzaldehyde (42.2 mg), acetic acid (17.2 µl), triethylamine (27.9 µl) and THF (1 ml), and the reaction mixture was stirred at room temperature for 12 h. The polymer-bound reagent was filtered off and the solvent was removed in vacuo. The residue was purified by preparative HPLC. The product with the molecular weight of 411.18 (C22H26ClN5O) was obtained in this way; MS (ESI): 412.23 (M+H+).

EXAMPLE 112

[1-(4-{5-[(4-Methoxybenzylamino)methyl][1,2,4]oxadiazol-3-yl}phenyl)pyrrolidin-3-y]dimethylamine

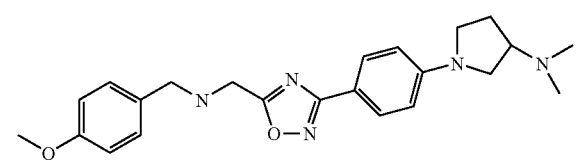

{1-[4-(5-aminomethyl[1,2,4]oxadiazol-3-yl)phenyl)pyrrolidin-3-yl}dimethylamine was reacted with p-anisaldehyde by method D. The product with the molecular weight of 407.23 (C23H29N5O2) was obtained in this way; MS (ESI): 408.30 (M+H+).

EXAMPLE 113

(1-{4-[5-(4-Fluorobenzyloxymethyl)[1,2,4]oxadiazol-3-yl]phenyl}pyrrolidin-3-yl)dimethylamine

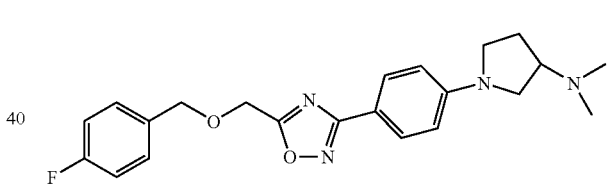

4-Fluorobenzyl bromide (18.9 mg) and potassium carbonate (27.6 mg) were added to a mixture of {3-[4-(3-dimethylaminopyrrolidin-1-yl)phenyl][1,2,4]oxadiazol-5-yl}methanol (28.8 mg) and DMF (0.3 ml). The reaction mixture was stirred at 60° C. for 3 h, filtered and purified by preparative HPLC. The product with the molecular weight of 396.20 (C22H25FN4O2) was obtained in this way; MS (ESI): 397.27 (M+H+).

{3-[4-(3-Dimethylaminopyrrolidin-1-yl)phenyl][1,2, 4]oxadiazol-5-yl}methanol

PyBOP (546.4 mg), HOAt (136.1 mg) and triethylamine (0.139 ml) were added to a mixture of 4-(3-dimethylaminopyrrolidin-1-yl)-N-hydroxybenzamidine (248.3 mg), benzyloxyacetic acid (0.143 ml) and DMF (3.0 ml) at 0° C., and the mixture was stirred at this temperature for 10 min. It was subsequently stirred at room temperature for 1 h, and then ethyl acetate and water were added to the reaction solution. The organic phase was then washed twice each with 10% strength citric acid solution, saturated sodium bicarbonate solution and water and dried over sodium sulfate, and the solvent was removed in vacuo.

The residue was then taken up in 3 ml of THF, and EDC (170.8 mg) and triethylamine (0.139 ml) were added, and the mixture was stirred at 80° C. for 16 h. Ethyl acetate and water were then added to the reaction solution. The organic phase was then washed twice each with 10% strength citric acid solution, saturated sodium bicarbonate solution and water and dried over sodium sulfate, and the solvent was removed in vacuo.

The residue was dissolved in methylene chloride (4.4 ml), and the solution was cooled to −78° C. At this temperature, a 1M boron trichloride solution (3 ml) was added. The reaction was allowed to warm to room temperature overnight, and then ethyl acetate and water were added. The product with the molecular weight of 288.2 (C15H20N4O2) was obtained in this way; MS (ESI): 289.2 (M+H+).

The following examples could be synthesized analogously:

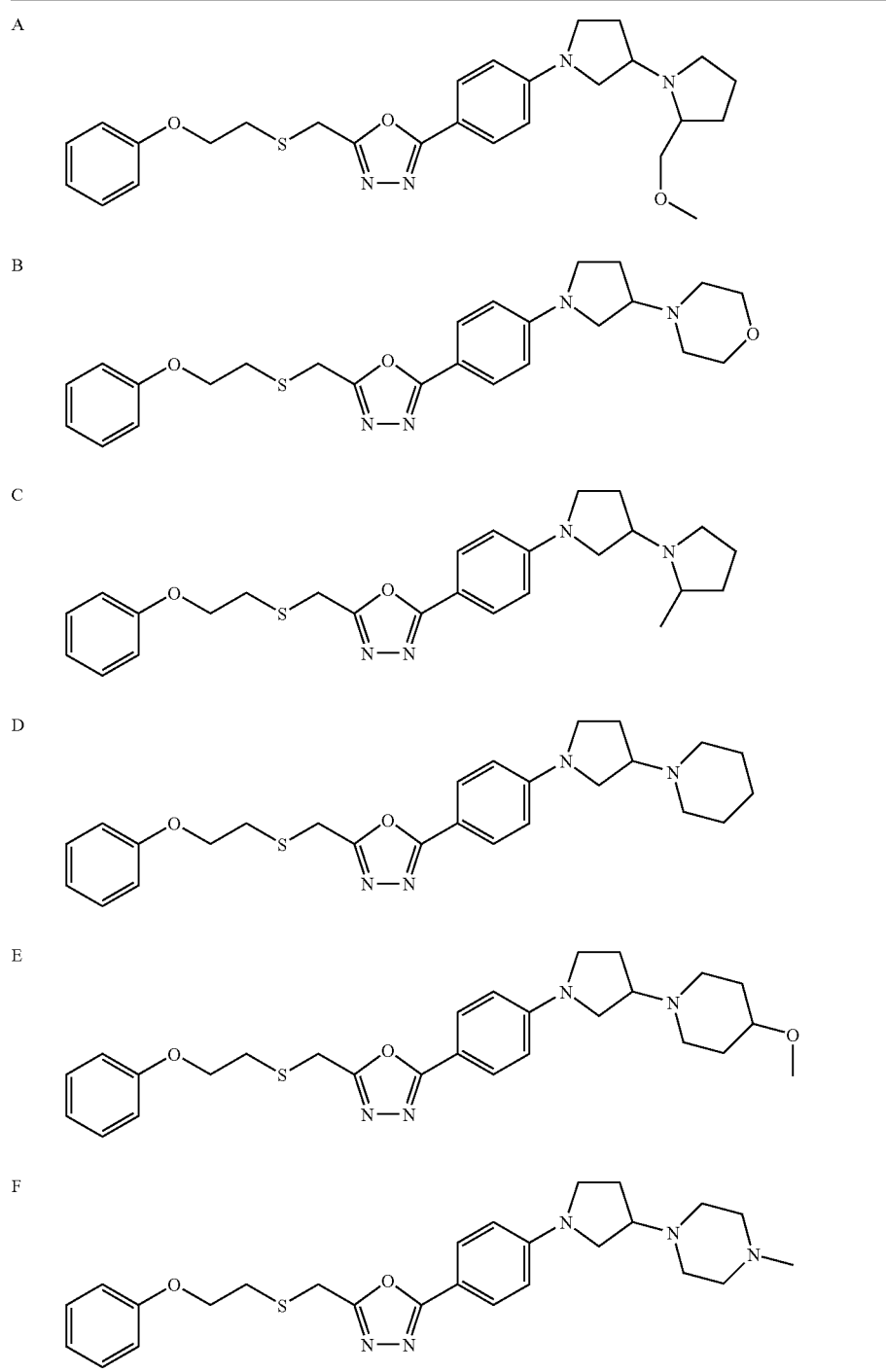

-continued
G
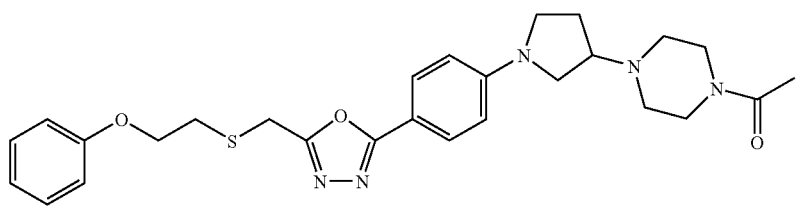
H
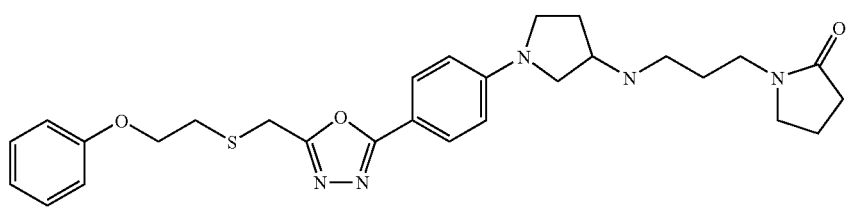
I
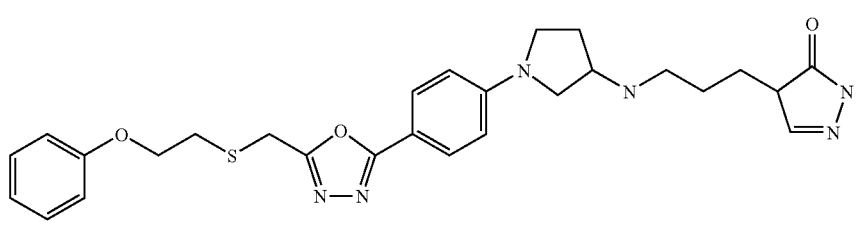
K
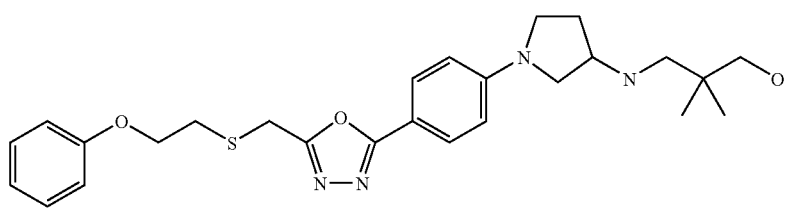
L
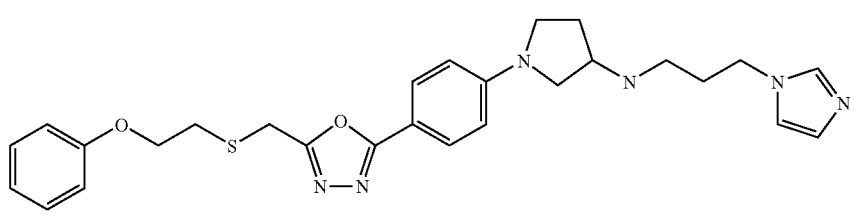
M
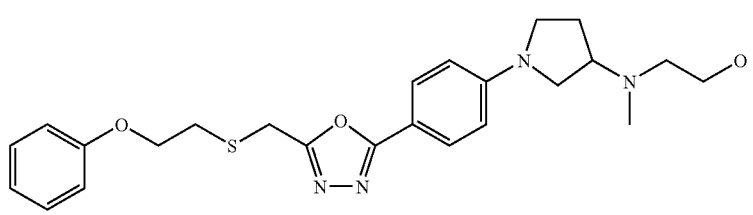
N
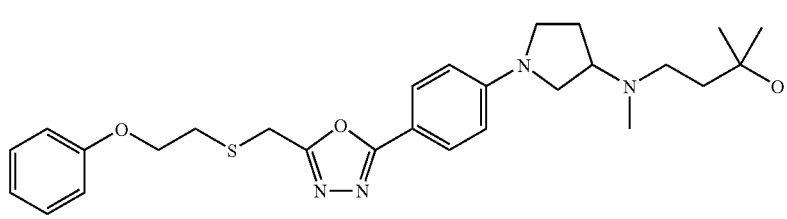

-continued
O
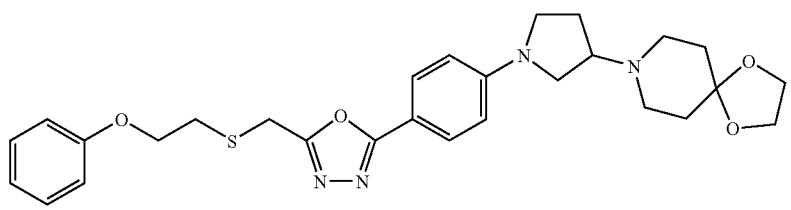
P
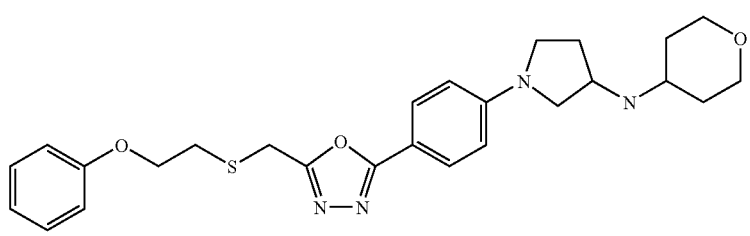
Q
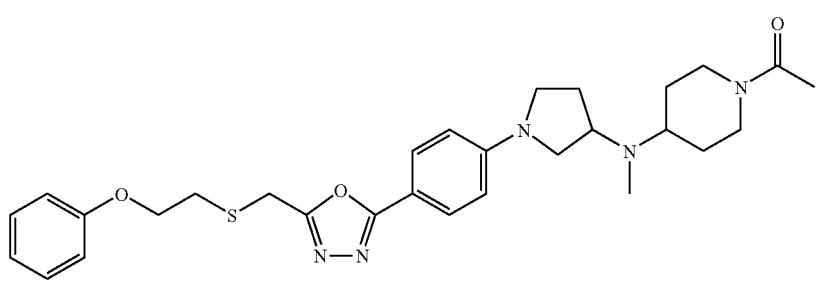
R
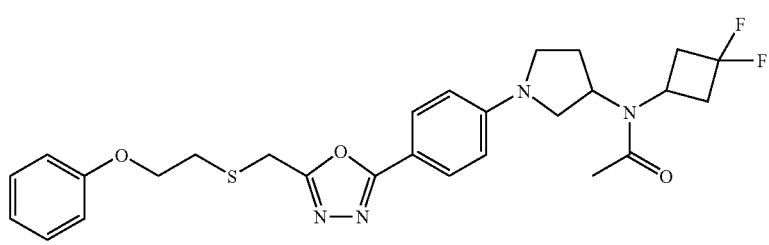
S
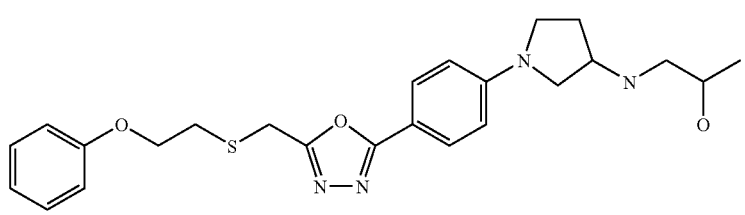
T
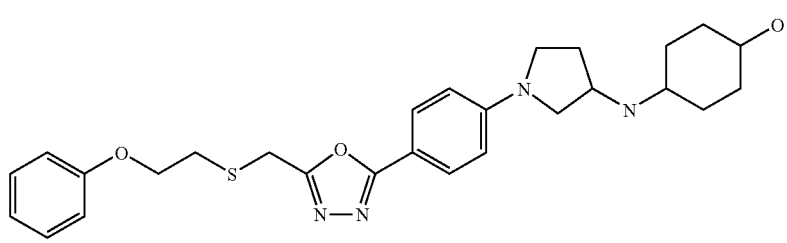

-continued
U
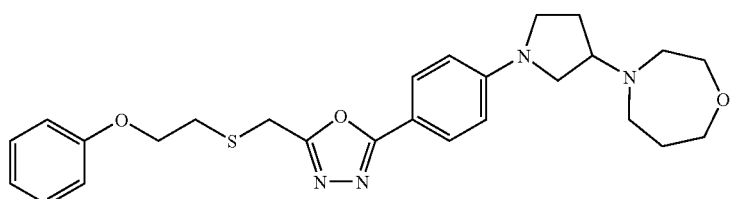
V
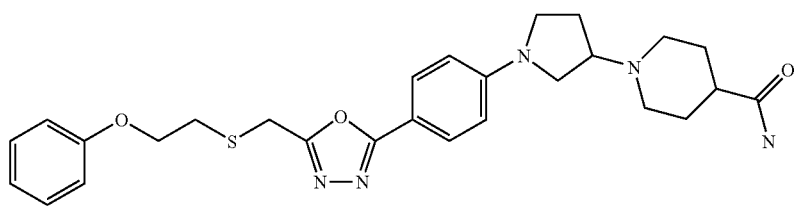
W
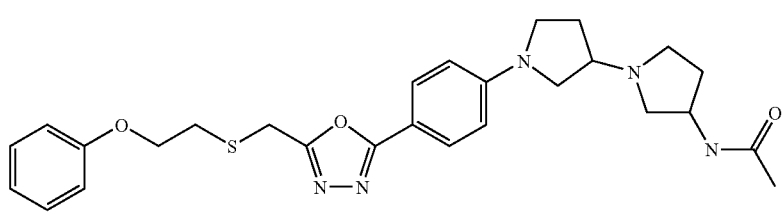
X
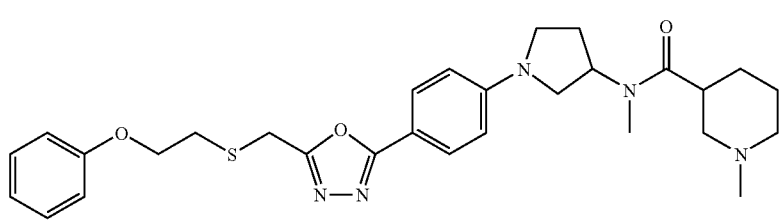
Y
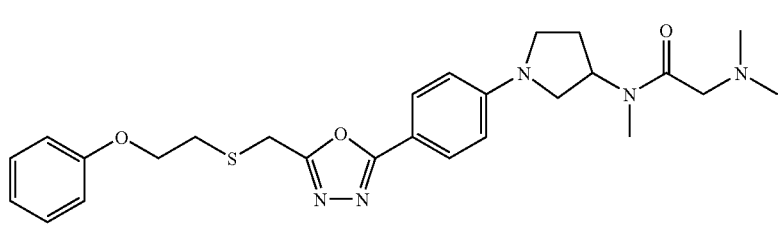
Z
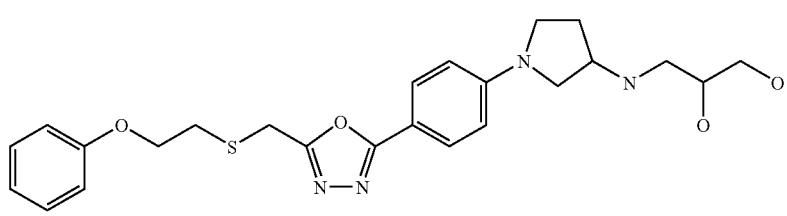
AA
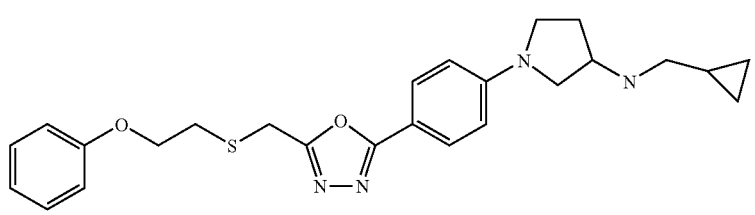

-continued
AB
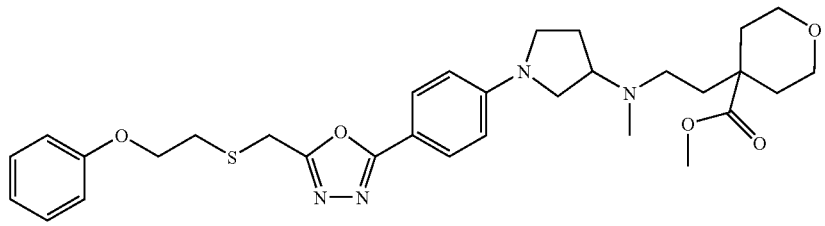
AC
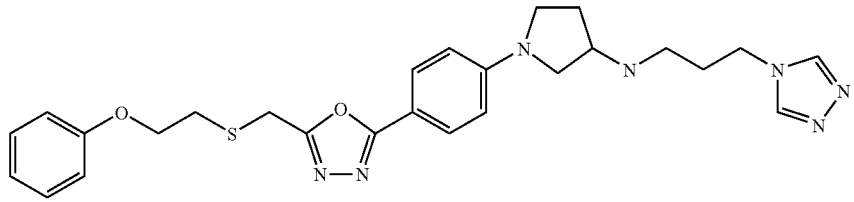
AD
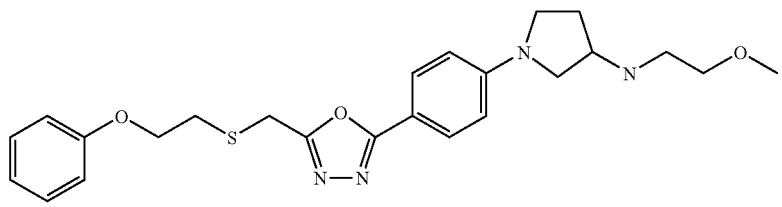
AE
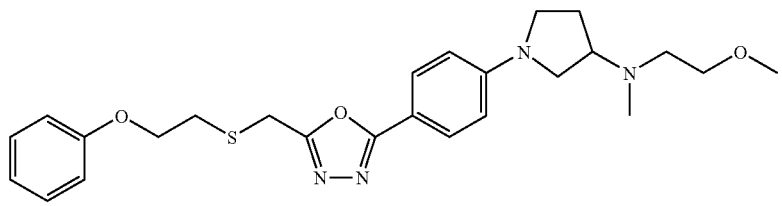
AF
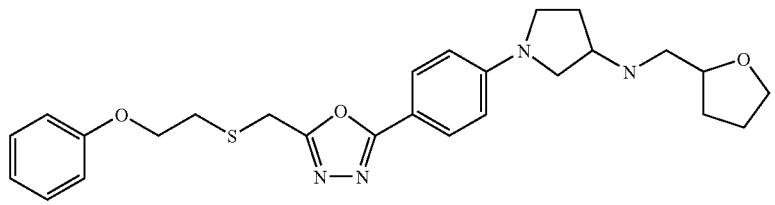
AG
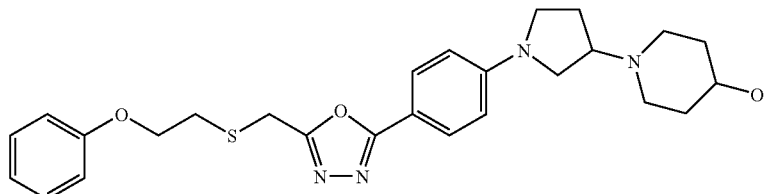
AH
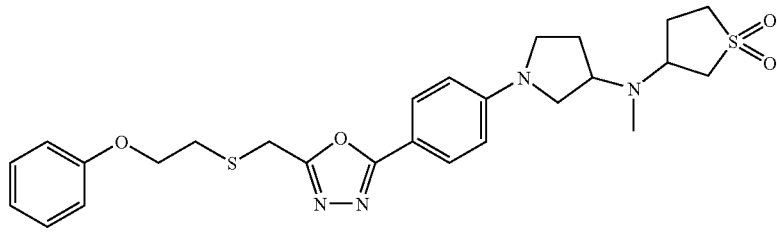

-continued

AI

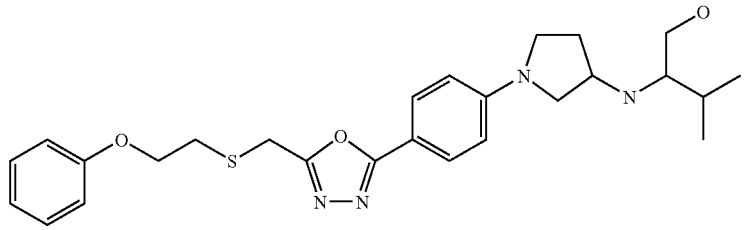

The invention claimed is:
1. A compound of the formula I,

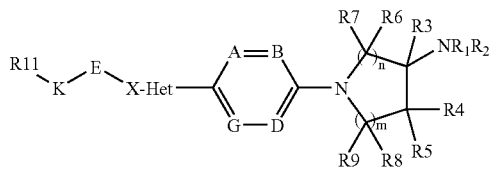

in which the meanings are

R1, R2 independently of one another H, $(C_1$-$C_8)$-alkyl, —$(CR13R14)_o$—R12, $(C_1$-$C_4)$-alkoxy-$(C_1$-$C_4)$-alkyl, $(C_3$-$C_8)$-alkenyl, $(C_3$-$C_8)$-alkynyl, CO—$(C_1$-$C_8)$-alkyl, —CO—$(CH_2)_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, $CF_3$, $NO_2$, CN, $(C_1$-$C_6)$-alkyl, O—$(C_1$-$C_8)$-alkyl, $(C_1$-$C_4)$-alkoxy-$(C_1$-$C_4)$-alkyl, hydroxy-$(C_1$-$C_4)$-alkyl, $(C_0$-$C_8)$-alkylene-aryl, oxo, CO(R22), CON(R23)(R24), hydroxy, COO(R25), N(R26)CO($C_1$-$C_6$)-alkyl, N(R27)(R28) or $SO_2CH_3$;

o 0, 1, 2, 3, 4, 5, 6;
q, s independently of one another 0, 1, 2, 3, 4;
R15, R16, R17, R18, R19, R20, R21, R22, R23, R24, R25, R26, R27, R28 independently of one another H, $(C_1$-$C_6)$-alkyl;
R17 and R18, R23 and R24, R27 and R28 independently of one another optionally together with the nitrogen atom to which they are bonded a 5-6 membered ring which, apart from the nitrogen atom, may also include 0-1 further heteroatoms from the group of NH, N—(C1-C6)-alkyl, oxygen and sulfur;
R12 OH, O—$(C_1$-$C_6)$-alkyl, CN, COO(R29), CON(R30)(R31), N(R32)(R33), 3-12 membered mono-, bi- or spirocyclic ring which may comprise one or more heteroatoms from the group of N, O and S, and the 3-12 membered ring may comprise further substituents such as F, Cl, Br, I, OH, $CF_3$, $NO_2$, CN, $OCF_3$, oxo, O—$(C_1$-$C_6)$-alkyl, $(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, $(C_2$-$C_6)$-alkynyl, O—$(C_0$-$C_8)$-alkylene-aryl, $(C_0$-$C_8)$-alkylene-aryl, N(R34)(R35), CO($C_1$-$C_6$)-alkyl, COO(R36) and S(O)$_u$ (R37);
u 0, 1, 2;

R34, R35 independently of one another H, $(C_1$-$C_8)$-alkyl;
R34 and R35 optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur, and optionally be substituted by 1-2 oxo groups;
R36, R37 H, $(C_1$-$C_8)$-alkyl;
R13, R14 independently of one another H, $(C_1$-$C_8)$-alkyl, hydroxy-$(C_1$-$C_4)$-alkyl, OH, $(C_1$-$C_4)$-alkoxy-$(C_1$-$C_4)$-alkyl;
R29, R30, R31 independently of one another H, $(C_1$-$C_8)$-alkyl, $(C_2$-$C_6)$-alkenyl, $(C_0$-$C_8)$-alkylene-aryl;
R32, R33 independently of one another H, $(C_1$-$C_6)$-alkyl or
R32 and R33 optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur and optionally be substituted by 1-2 oxo groups;
R3 H, $(C_1$-$C_6)$-alkyl;
R4, R5 independently of one another H, $(C_1$-$C_6)$-alkyl, OH, O—$(C_1$-$C_6)$-alkyl, O—CO($C_1$-$C_6$)-alkyl, S—($C_1$-$C_6$)-alkyl;
R6, R7, R8, R9 independently of one another H, $(C_1$-$C_8)$-alkyl, or
R6 and R7, R8 and R9 independently of one another optionally oxo;
n, m 1;
A, B, D, G C(R38);
R38 H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R39)(R40), $SO_2$—$CH_3$, COOH, COO—($C_1$-$C_6$)-alkyl, CON(R41)(R42), N(R43)CO(R44), N(R45)$SO_2$(R46), CO(R47), —(CR48R49)$_x$—O(R50);
R39, R40, R41, R42, R43, R45 independently of one another H, $(C_1$-$C_8)$-alkyl; or
R39 and R40, R41 and R42 independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur;
R44, R46, R47 independently of one another H, $(C_1$-$C_8)$-alkyl, aryl;
R48, R49 independently of one another H, $(C_1$-$C_8)$-alkyl;
R50 H, $(C_1$-$C_6)$-alkyl;

x 1, 2, 3, 4;

Het 1,3,4-oxadiazolyl;

X a bond, a group of the formula —(CR51R52)$_y$— in which one or more —(CR51R52)— groups may be replaced by Y C=C, C≡C;

Y O, S, N(R53), CO, SO, SO$_2$;

R51, R52 independently of one another H, (C$_1$-C$_4$)-alkyl, where R51 and R52 in the y groups may in each case have the same or different meanings;

y 1, 2, 3, 4, 5, 6;

R53 H, (C$_1$-C$_8$)-alkyl;

E 3-14 membered bivalent carbo- or heterocyclic ring structure having 0-4 heteroatoms from the group of N, O and S, which may optionally have substituents from the group of H, F, Cl, Br, I, OH, CF$_3$, NO$_2$, CN, OCF$_3$, oxo, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, (C$_0$-C$_8$)-alkylene-aryl, O—(C$_0$-C$_8$)-alkylene-aryl, S-aryl, N(R54)(R55), SO$_2$—CH$_3$, COOH, COO—(C$_1$-C$_6$)-alkyl, CON(R56)(R57), N(R58)CO(R59), N(R60)SO$_2$(R61), CO(R62) and be mono- or bicyclic;

R54, R55, R56, R57, R58, R60 independently of one another H, (C$_1$-C$_8$)-alkyl;

R54 and R55, R56 and R57 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;

R59, R61, R62 independently of one another H, (C$_1$-C$_8$)-alkyl, aryl;

K a bond, a group of the formula —(CR63R64)$_z$— in which one or more —(CR63R64)-groups may be replaced by Z, C≡C, C=C;

Z O, S, N(R65), CO, SO, SO$_2$;

R63, R64 independently of one another H, (C$_1$-C$_8$)-alkyl, hydroxy, (C$_1$-C$_6$)-alkoxy, where R63 and R64 in the z groups may in each case have the same or different meanings;

z 1, 2, 3, 4, 5, 6;

R65 H, (C$_1$-C$_8$)-alkyl;

R11 H, (C$_1$-C$_8$)-alkyl, (C$_1$-C$_4$)-alkoxy-(C$_1$-C$_4$)-alkyl, (C$_3$-C$_8$)-alkenyl, (C$_3$-C$_8$)-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, CF$_3$, NO$_2$, CN, (C$_1$-C$_6$)-alkyl, O—(C$_1$-C$_6$)-alkyl, (C$_1$-C$_4$)-alkoxy-(C$_1$-C$_4$)-alkyl, (C$_0$-C$_8$)-alkylene-aryl, oxo, CO(R66), CON(R67)(R68), hydroxy, hydroxy-(C$_1$-C$_4$)-alkyl, COO(R69), N(R70)CO(C$_1$-C$_6$)-alkyl, N(R71)(R72) or SO$_2$CH$_3$;

R66, R67, R68, R69, R70, R71, R72 independently of one another H, (C$_1$-C$_8$)-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur; or the N-oxides thereof and the physiologically tolerated salts thereof.

2. A compound of the formula I as claimed in claim 1, in which the meanings are R1, R2 independently of one another H, (C$_1$-C$_8$)-alkyl, —(CR13R14)$_o$—R12, (C$_1$-C$_4$)-alkoxy-(C$_1$-C$_4$)-alkyl, (C$_3$-C$_8$)-alkenyl, (C$_3$-C$_8$)-alkynyl, CO—(C$_1$-C$_8$)-alkyl, —CO—(CH$_2$)$_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, (C$_0$-C$_8$)-alkylene-aryl, oxo, CO(R22), CON(R23)(R24), hydroxy, COO(R25), N(R26)CO(C$_1$-C$_6$)-alkyl or N(R27)(R28);

R12 OH, O—(C$_1$-C$_6$)-alkyl, CN, COO(R29), CON(R30)(R31), N(R32)(R33), 3-12 membered mono-, bi- or spirocyclic ring which may comprise one or more heteroatoms from the group of N, O and S, and the 3-12 membered ring may comprise further substituents such as F, Cl, Br, I, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, (C$_2$-C$_6$)-alkynyl, O—(C$_0$-C$_8$)-alkylene-aryl, (C$_0$-C$_8$)-alkylene-aryl, N(R34)(R35), CO(C$_1$-C$_6$)-alkyl and COO(R36); and R6, R7, R8, R9 independently of one another H, (C$_1$-C$_8$)-alkyl;

where the remaining variables for formula I are as defined in claim 1.

3. A compound of the formula I as claimed in claim 1, in which the meanings are R1, R2 independently of one another H, (C$_1$-C$_8$)-alkyl, —(CR13R14)$_o$—R12, (C$_1$-C$_4$)-alkoxy-(C$_1$-C$_4$)-alkyl, (C$_3$-C$_8$)-alkenyl, CO—(C$_1$-C$_8$)-alkyl, —CO—(CH$_2$)$_o$—R12, CO(C(R15)(R16))$_q$N(R17)(R18), CO(C(R19)(R20))$_s$O(R21); or R1 and R2 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, CF$_3$, (C$_1$-C$_6$)-alkyl, O—(C$_1$-C$_4$)-alkyl, (C$_1$-C$_4$)-alkoxy-(C$_1$-C$_4$)-alkyl, hydroxy-(C$_1$-C$_4$)-alkyl, (C$_0$-C$_2$)-alkylene-aryl, oxo, CO(R22), CON(R23)(R24), hydroxy, COO(R25), N(R26)CO(C$_1$-C$_6$)-alkyl, N(R27)(R28) or SO$_2$CH$_3$;

o 0, 1, 2, 3, 4, 5, 6;

q 1, 2, 3;

s 0, 1, 2, 3, 4;

R15, R16, R17, R18, R19, R20, R21, R22, R23, R24, R25, R26, R27, R28 independently of one another H, (C$_1$-C$_6$)-alkyl; or R17 and R18, R23 and R24, R27 and R28 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;

R12 OH, O—(C$_1$-C$_6$)-alkyl, CN, COO(R29), CON(R30)(R31), 3-12 membered mono-, bi- or spirocyclic ring which may comprise one or more heteroatoms from the group of N, O and S, and the 3-12 membered ring may comprise further substituents such as F, Cl, Br, OH, CF$_3$, CN, oxo, O—(C$_1$-C$_6$)-alkyl, (C$_1$-C$_4$)-alkoxy-(C$_1$-C$_4$)-alkyl, (C$_1$-C$_6$)-alkyl, O—(C$_0$-C$_8$)-alkylene-aryl, (C$_0$-C$_8$)-alkylene-aryl, N(R34)(R35), CO(C$_1$-C$_6$)-alkyl, COO(R36), S(O)$_u$(R37);

u 0, 1, 2;

R34, R35 independently of one another H, (C$_1$-C$_8$)-alkyl; or

R34 and R35 optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur, and optionally be substituted by 1-2 oxo groups;

R36, R37 H, (C$_1$-C$_8$)-alkyl;

R13, R14 independently of one another H, (C$_1$-C$_8$)-alkyl, hydroxy-(C$_1$-C$_4$)-alkyl, OH, (C$_1$-C$_4$)-alkoxy-(C$_1$-C$_4$)-alkyl;

R29, R30, R31 independently of one another H, (C$_1$-C$_8$)-alkyl;

R3 H, (C$_1$-C$_6$)-alkyl;

R4, R5 independently of one another H, (C$_1$-C$_6$)-alkyl, OH, O—(C$_1$-C$_6$)-alkyl, O—CO(C$_1$-C$_6$)-alkyl, S—(C$_1$-C$_6$)-alkyl;

R6, R7, R8, R9 H; or

R6 and R7, R8 and R9 independently of one another optionally oxo;

n 1;

m 1;

A, B, D, G C(R38); or the groups A and B or D and G are in each case C(R38) and together form an ortho-phenylene unit so that the overall result is a 1,4-bisubstituted naphthalene system;

R38 H, F, Cl, Br, CF$_3$, CN, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_0$-C$_8$)-alkylene-aryl, O—(C$_0$-C$_8$)-alkylene-aryl, N(R39)(R40), SO$_2$—CH$_3$, CON(R41)(R42), N(R43)CO(R44), CO(R47), —(CR48R49)$_x$—O(R50);

R39, R40, R41, R42, R43 independently of one another H, (C$_1$-C$_8$)-alkyl; or

R39 and R40, R41 and R42 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;

R44, R47 independently of one another H, (C$_1$-C$_8$)-alkyl, aryl;

R48, R49 H;

R50 H, (C$_1$-C$_6$)-alkyl;

x 1, 2;

Het is

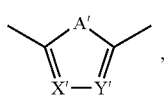

in which

A' is O,

X', Y' are;

X a bond, a group of the formula —(CR51R52)$_y$—, in which one or more —(CR51R52)-groups may be replaced by Y, C═C, C≡C;

R51, R52 independently of one another H, (C$_1$-C$_4$)-alkyl, where R51 and R52 in the y groups may in each case have the same or different meanings;

Y O, S, N(R53), CO;

R53 H, (C$_1$-C$_8$)-alkyl;

E 3-8 membered bivalent carbo- or heterocyclic ring structure having 0-4 heteroatoms from the group of N, O and S, which may optionally have substituents from the group of H, F, Cl, Br, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, O—(C$_3$-C$_8$)-cycloalkyl, (C$_2$-C$_6$)-alkynyl, (C$_0$-C$_8$)-alkylene-aryl, O—(C$_0$-C$_8$)-alkylene-aryl, S-aryl, N(R54)(R55), SO$_2$—CH$_3$, N(R58)CO(R59), N(R60)SO$_2$(R61), CO(R62) and be mono- or bicyclic;

R54, R55, R58, R60 independently of one another H, (C$_1$-C$_8$)-alkyl;

R59, R61, R62 independently of one another H, (C$_1$-C$_8$)-alkyl, aryl;

K O, a bond, CH$_2$O, OCH$_2$, S, SO, SO$_2$, N(R80), N(R81)CO, CON(R82), (C(R83)(R84))$_v$, CO, C═C, C≡C, SCH$_2$, SO$_2$CH$_2$;

v 1, 2, 3, 4;

R80, R81, R82, R83, R84 independently of one another H, (C$_1$-C$_8$)-alkyl;

R11 H, (C$_1$-C$_8$)-alkyl, (C$_1$-C$_4$)-alkoxy-(C$_1$-C$_4$)-alkyl, (C$_3$-C$_8$)-alkenyl, (C$_3$-C$_8$)-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, (C$_0$-C$_8$)-alkylene-aryl, oxo, CO(R66), CON(R67)(R68), hydroxy, COO(R69), N(R70)CO(C$_1$-C$_6$)-alkyl, N(R71)(R72) or SO$_2$CH$_3$;

R66, R67, R68, R69, R70, R71, R72 independently of one another H, (C$_1$-C$_8$)-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur; or the N-oxides thereof and the physiologically tolerated salts thereof.

4. A compound of the formula I as claimed in claim 1 or 3, in which the meanings are:

R1, R2 independently of one another H, (C$_1$-C$_8$)-alkyl, —(CR13R14)$_o$—R12, (C$_1$-C$_4$)-alkoxy-(C$_1$-C$_4$)-alkyl, CO—(C$_1$-C$_8$)-alkyl, —CO—(CH$_2$)$_o$—R12, CO(C(R15)(R16))$_q$N(R17)(R18), CO(C(R19)(R20))$_o$O(R21); or R1 and R2 form together with the nitrogen atom to which they are bonded a 4 to 10-membered mono- or bicyclic ring which, apart from the nitrogen atom, may include 0 to 2 additional heteroatoms selected from the group of oxygen, nitrogen and sulfur, where the heterocyclic ring system may additionally be substituted by F, Cl, CF$_3$, (C$_1$-C$_6$)-alkyl, O—(C$_1$-C$_4$)-alkyl, (C$_1$-C$_4$)-alkoxy-(C$_1$-C$_4$)-alkyl, (C$_0$-C$_2$)-alkylene-aryl, oxo, CO(R22), hydroxy, N(R27)(R28) or SO$_2$CH$_3$;

o 0, 1, 2, 3, 4;

q 1 or 2;

s 0, 1, 2, 3;

R15, R16, R17, R18, R19, R20, R21, R22, R27, R28 independently of one another H, (C$_1$-C$_6$)-alkyl; or R17 and R18, R27 and R28 independently of one another optionally together with the nitrogen atom to which they are bonded a 5-6 membered ring selected from pyrrolidine, piperidine, N-methylpiperazine and morpholine;

R12 OH, O—($C_1$-$C_6$)-alkyl, CN, 3-10 membered mono- or bicyclic ring which may comprise 1-3 heteroatoms from the group of N, O and S, and the 3-10 membered ring may comprise further substituents such as F, Cl, Br, OH, $CF_3$, CN, oxo, O—($C_1$-$C_6$)-alkyl, ($C_1$-$C_4$)-alkoxy-($C_1$-$C_4$)-alkyl, ($C_1$-$C_6$)-alkyl, ($C_0$-$C_2$)-alkylene-aryl, N(R34)(R35), CO($C_1$-$C_6$)-alkyl;

u 0 or 2;

R34, R35 independently of one another H, ($C_1$-$C_8$)-alkyl; or

R34 and R35 optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur, and optionally be substituted by 1-2 oxo groups;

R36, R37 H, ($C_1$-$C_8$)-alkyl;

R13, R14 independently of one another H, ($C_1$-$C_8$)-alkyl, hydroxy-($C_1$-$C_4$)-alkyl, OH, ($C_1$-$C_4$)-alkoxy-($C_1$-$C_4$)-alkyl;

R3 H;

R4, R5 independently of one another H, ($C_1$-$C_6$)-alkyl, OH, O—($C_1$-$C_6$)-alkyl, O—CO($C_1$-$C_6$)-alkyl;

R6, R7, R8, R9 H;

n 1 m 1;

A, B, D, G C(R38);

R38 H, F, Cl, Br, $CF_3$, CN, O—($C_1$-$C_6$)-alkyl, ($C_1$-$C_6$)-alkyl, $SO_2$—$CH_3$, CON(R41)(R42), N(R43)CO(R44), CO(R47), —(CR48R49)$_x$—O(R50);

R41, R42, R43 independently of one another H, ($C_1$-$C_8$)-alkyl; or

R39 and R40, R41 and R42 independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur;

R47 H, ($C_1$-$C_8$)-alkyl;

R48, R49 H;

R50 H, ($C_1$-$C_6$)-alkyl;

x 1;

Het 1,3,4-oxadiazolyl;

X a bond, $CH_2$—$CH_2$, $CH_2$Y, $YCH_2$, (R75)$YCH_2$, $CH_2$—NCO(R75), $CH_2$CON(R75); C(R76)(R77), C(R78)(R79)O, N(R75), C=C, C≡C;

Y O, S, N(R53);

R53 H, ($C_1$-$C_8$)-alkyl;

R75, R76, R77, R78, R79 independently of one another H, ($C_1$-$C_8$)-alkyl;

E 5-7 membered bivalent carbo- or heterocyclic ring structure having 0-3 heteroatoms from the group of N, O and S, which may optionally have substituents from the group of H, F, Cl, Br, OH, $CF_3$, $NO_2$, CN, $OCF_3$, O—($C_1$-$C_6$)-alkyl, S—($C_1$-$C_6$)-alkyl, ($C_1$-$C_6$)-alkyl, ($C_2$-$C_6$)-alkenyl, O—($C_0$-$C_8$)-alkylene-aryl, S-aryl, N(R54)(R55), $SO_2$—$CH_3$, N(R58)CO(R59), CO(R62) and be mono- or bicyclic;

R54, R55, R58 independently of one another H, ($C_1$-$C_8$)-alkyl;

R59, R62 independently of one another H, ($C_1$-$C_8$)-alkyl;

K O, a bond, $CH_2$O, $OCH_2$, N(R80), N(R81)CO, CON(R82), (C(R83)(R84))$_v$, CO, C≡C, $SCH_2$;

v 1, 2, 3;

R80, R81, R83, R84 independently of one another H, ($C_1$-$C_8$)-alkyl;

R11 ($C_1$-$C_8$)-alkyl, ($C_1$-$C_4$)-alkoxy-($C_1$-$C_4$)-alkyl, a 3 to 10-membered mono-, bi- or spirocyclic ring which may include 0 to 3 heteroatoms selected from the group of oxygen, nitrogen and sulfur, where the ring system may additionally be substituted by F, Cl, Br, $CF_3$, CN, ($C_1$-$C_6$)-alkyl, O—($C_1$-$C_8$)-alkyl, ($C_0$-$C_2$)-alkylene-aryl, oxo, CO(R66), CON(R67)(R68), hydroxy, N(R70)CO($C_1$-$C_6$)-alkyl, N(R71)(R72) or $SO_2CH_3$;

R66, R67, R68, R70, R71, R72 independently of one another H, ($C_1$-$C_8$)-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur; or the N-oxides thereof and the physiologically tolerated salts thereof.

5. A compound of the formula I as claimed in claim 1, 2 or 3, in which radicals R1, R2, R11, R38 and the groups X, E and K have the following meanings:

R1, R2 independently of one another H, ($C_1$-$C_8$)-alkyl, —(CR13R14)$_o$—R12, ($C_1$-$C_4$)-alkoxy-($C_1$-$C_4$)-alkyl, or R1 and R2 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by ($C_1$-$C_6$)-alkyl, O—($C_1$-$C_4$)-alkyl, ($C_1$-$C_4$)-alkoxy-($C_1$-$C_4$)-alkyl, hydroxy-($C_1$-$C_4$)-alkyl, ($C_0$-$C_2$)-alkylene-aryl, oxo, CO(R22), CON(R23)(R24), hydroxy, N(R27)(R28) or $SO_2CH_3$;

o 0, 1, 2, 3, 4;

R22, R23, R24, R27, R28 independently of one another H, ($C_1$-$C_6$)-alkyl; or

R23 and R24, R27 and R28 independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur;

R12 OH, O—($C_1$-$C_6$)-alkyl, CN 3-12 membered mono-, bi- or spirocyclic ring which may comprise 1 to 3 heteroatoms from the group of N, O and S, and the 3-12 membered ring may comprise further substituents such as F, OH, $CF_3$, CN, oxo, ($C_1$-$C_6$)-alkyl, ($C_0$-$C_2$)-alkylene-aryl, N(R34)(R35), COO(R36), CO($C_1$-$C_6$)-alkyl;

R34, R35 independently of one another H, ($C_1$-$C_4$)-alkyl;

R36 H, ($C_1$-$C_6$)-alkyl, ($C_0$-$C_2$)-alkylene-aryl;

R13, R14 independently of one another H, ($C_1$-$C_8$)-alkyl, hydroxy-($C_1$-$C_4$)-alkyl, OH, ($C_1$-$C_4$)-alkoxy-($C_1$-$C_4$)-alkyl;

R38 H, F, Cl, Br, $CF_3$, CN, ($C_1$-$C_6$)-alkyl;

X a bond, $CH_2CH_2$, C(R76)(R77), N(R75), C=C, (R75)$YCH_2$, $CH_2$—NCO(R75), $CH_2$CON(R75);

Y O, S, N(R53), CO

R75, R76, R77 independently of one another H, ($C_1$-$C_8$)-alkyl;

R53 H, ($C_1$-$C_8$)-alkyl;

E 5-7 membered bivalent carbo- or heterocyclic ring structure having 0-3 heteroatoms from the group of N, O and S, which may optionally have substituents from the group of H, F, Cl, Br, $CF_3$, OH, CN, $OCF_3$, O—$(C_1-C_6)$-alkyl, $(C_1-C_6)$-alkyl, $SO_2$—$CH_3$, CO(R65);

R65 H, $(C_1-C_8)$-alkyl;

K O, a bond, $CH_2O$, $CH_2$, $OCH_2$, S, $SO_2$, N(R80), N(R81)CO, CON(R82), $(C(R83)(R84))_v$, CO, C≡C, $SCH_2$, $SO_2CH_2$;

v 1, 2, 3;

R80, R81, R82, R83, R84 independently of one another H, $(C_1-C_8)$-alkyl;

R11 $(C_1-C_8)$-alkyl, $(C_1-C_4)$-alkoxy-$(C_1-C_4)$-alkyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, $CF_3$, CN, $(C_1-C_6)$-alkyl, O—$(C_1-C_8)$-alkyl, oxo, CO(R66), hydroxy, N(R70)CO($C_1-C_6$)-alkyl, or $SO_2CH_3$;

R66, R70 independently of one another H, $(C_1-C_8)$-alkyl; the N-oxides thereof and the physiologically tolerated salts thereof.

6. A medicament comprising one or more of the compounds as claimed in claim 1.

7. A medicament comprising one or more of the compounds as claimed in claim 1 and one or more anorectic active ingredients.

8. A process for producing a medicament comprising one or more of the compounds of the formula I as claimed in claim 1, which comprises mixing the active ingredient with a pharmaceutically suitable carrier, and converting this mixture into a form suitable for administration.

9. A compound of the formula I as claimed in claim 4, in which the meanings are:

R1, R2 independently of one another H, $(C_1-C_8)$-alkyl, —$(CR13R14)_o$—R12, $(C_1-C_4)$-alkyl, CO—$(C_1-C_8)$-alkyl, —CO—$(CH_2)_o$—R12, CO(C(R15)(R16))$_q$N(R17)(R18), or R1 and R2 form together with the nitrogen atom to which they are bonded a 4 to 10-membered mono- or bicyclic ring which, apart from the nitrogen atom, may include 0 to 2 additional heteroatoms selected from the group of oxygen and nitrogen, where the heterocyclic ring system may additionally be substituted by F, $(C_1-C_6)$-alkyl, $(C_1-C_4)$-alkoxy-$(C_1-C_4)$-alkyl, oxo, CO(R22), hydroxy, N(R27)(R28);

o 0, 1, 2, 3;

q 1 or 2;

s 0, 1, 2;

R15, R16, R17, R18, R19, R20, R21, R22, R27, R28 independently of one another H, $(C_1-C_6)$-alkyl; or R17 and R18, R27 and R28 independently of one another optionally together with the nitrogen atom to which they are bonded a 5-6 membered ring selected from pyrrolidine, piperidine, N-methylpiperazine and morpholine;

R12 OH, O—$(C_1-C_6)$-alkyl, 3-10 membered mono- or bicyclic ring which may comprise 1-2 hetero atoms from the group of N, O and S, and the 3-10 membered ring may comprise further substituents such as F, OH, oxo, $(C_1-C_6)$-alkyl, CO($C_1-C_6$)-alkyl;

u 2;

R34, R35 independently of one another H, $(C_1-C_5)$-alkyl; or

R34 and R35 optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur, and optionally be substituted by 1-2 oxo groups;

R36, R37 H, $(C_1-C_8)$-alkyl;

R13, R14 independently of one another H, $(C_1-C_8)$-alkyl, hydroxy-$(C_1-C_4)$-alkyl, OH, $(C_1-C_4)$-alkoxy-$(C_1-C_4)$-alkyl;

R3 H;

R4, R5 independently of one another H, OH, O—$(C_1-C_6)$-alkyl;

R6, R7, R8, R9 H;

n 1 m 1;

A,B,D,G C(R38);

R38 H, F, Cl, $CF_3$, CN, $(C_1-C_6)$-alkyl, —$(CR48R49)_x$—O(R50);

R41, R42, R43 independently of one another 1-I, $(C_1-C_8)$-alkyl; or

R39 and R40, R41 and R42 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R47 H, $(C_1-C_8)$-alkyl;

R48, R49 H; R50 H, $(C_1-C_6)$-alkyl;

x 1;

Het 1,3,4-oxadiazolyl;

X a bond, $CH_2$—$CH_2$, C(R76)(R77), N(R75), $CH_2Y$, $CH_2Y$(R75), $CH_2$—NCO(R75), $CH_2$—CON(R75); C=C;

Y O, S, N(R53);

R53 H, $(C_1-C_8)$-alkyl;

R75, R76, R77, R78, R79 independently of one another H, $(C_1-C_8)$-alkyl;

E 5-7 membered bivalent carbo- or heterocyclic ring structure having 0-2 heteroatoms from the group of N, O and S, which may optionally have substituents from the group of H, F, Cl, Br, OH, $CF_3$, $NO_2$, $OCF_3$, O—$(C_1-C_6)$-alkyl, $(C_1-C_6)$-alkyl, $(C_2-C_6)$-alkenyl, N(R54)(R55), $SO_2$—$CH_3$, CO(R62), and which is monocyclic;

R54, R55, R58 independently of one another H, $(C_1-C_8)$-alkyl;

R59, R62 independently of one another H, $(C_1-C_8)$-alkyl;

K O, a bond, $CH_2O_1$ $OCH_2$, CON(R82), $(C(R83)(R84))_v$, CO, C≡C;

v 1, 2;

R80, R81, R83, R84 independently of one another H, $(C_1-C_8)$-alkyl;

R11 preferably $(C_1C_8)$-alkyl, $(C_1-C_4)$-alkoxy-$(C_1-C_4)$-alkyl, a 3 to 10-membered mono- or bicyclic ring which may include 0 to 2 heteroatoms selected from the group of oxygen, nitrogen and sulfur, where the ring system may additionally be substituted by F, Cl, Br, $CF_3$, CN, $(C_1-C_6)$-alkyl, O—$(C_1-C_8)$-alkyl, oxo, CO(R66), CON(R67)(R68), N(R70)CO($C_1-C_6$)-alkyl, or $SO_2CH_3$;

R66, R67, R68, R70, R71, R72 independently of one another H, $(C_1$ -$C_8)$-alkyl; or R67 and R68, R71 and R72 independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur; or the N-oxides thereof and the physiologically tolerated salts thereof.

10. A compound of the formula I as claimed in claim 5, in which radicals R1, R2, R11, R38 and the groups X, E and K have the following meanings:

R1, R2 independently of one another H, $(C_1$-$C_8)$-alkyl, or R1 and R2 form together with the nitrogen atom to which they are bonded a 5 to 6-menibered monocyclic ring which, apart from the nitrogen atom, may include 0 to 1 additional heteroatoms selected from the group of oxygen, nitrogen and sulfur, where the heterocyclic ring system may additionally be substituted by $(C_1$-$C_6)$-alkyl;

o 0, 1, 2, 3, 4;

R22, R23, R24, R27, R28 independently of one another H, $(C_1$-$C_6)$-alkyl; or

R23 and R24, R27 and R28 independently of one another optionally together with the nitrogen atom to which they are bonded a 5-6 membered ring which, apart from the nitrogen atom, may also include 0-1 further heteroatoms from the group of NH, N—$(C_1$-$C_6)$-alkyl, oxygen and sulfur;

R12 OH, O—$(C_1$-$C_6)$-alkyl, CN 3-12 membered mono-, bi- or spirocyclic ring which may comprise 1 to 3 heteroatoms from the group of N, O and S, and the 3-12 membered ring may comprise further substituents such as F, OH, $CF_3$, CN, oxo, $(C_1$-$C_6)$-alkyl, $(C_0$-$C_2)$-alkylene-aryl, N(R34)(R35), COO(R36), CO($C_1$-$C_6)$-alkyl;

R34, R35 independently of one another H, $(C_1$-$C_4)$-alkyl;

R36 H, $(C_1$-$C_6)$-alkyl, $(C_0$-$C_2)$-alkylene-aryl;

R13, R14 independently of one another H, $(C_1$-$C_8)$-alkyl, hydroxy-$(C_1$-$C_4)$-alkyl, OH, $(C_1$-$C_4$-alkoxy-$(C_1$-$C_4)$-alkyl;

R38 H, F, Cl, Br, $CF_3$, CN, $(C_1$-$C_6)$-alkyl;

X a bond, $CH_2CH_2$, C(R76)(R77), N(R75), C=C, (R75)YCH$_2$, $CH_2$—NCO(R75), $CH_2$CON(R75);

Y O, S, N(R53), CO

R75, R76, R77 independently of one another H, $(C_1$-$C_8)$-alkyl;

R53 H, $(C_1$-$C_8)$-alkyl;

E 5-7 membered bivalent carbo- or heterocyclic ring structure having 0-3 heteroatoms from the group of N, O and S, which may optionally have substituents from the group of H, F, Cl, Br, $CF_3$, OH, CN, $OCF_3$, O—$(C_1$-$C_6)$-alkyl, $(C_1$-$C_6)$-alkyl, $SO_2$—$CH_3$, CO(R65);

R65 H, $(C_1$-$C_8)$-alkyl;

K O, a bond, $CH_2O$, $CH_2$, $OCH_2$, N(R80), C≡C;

v 1, 2, 3;

R80, R81, R82, R83, R84 independently of one another H, $(C_1$-$C_8)$-alkyl;

R11 $(C_1$-$C_8)$-alkyl, $(C_1$-$C_4)$-alkoxy-$(C_1$-$C_4)$-alkyl, a 3 to 10-membered mono-, bi- or spirocyclic ring which may include 0 to 4 heteroatoins selected from the group of oxygen, nitrogen and sulfur, where the ring system may additionally be substituted by F, Cl, Br, $CF_3$, CN, $(C_1$-$C_6)$-alkyl, O—$(C_1$-$C_6)$-alkyl, oxo, CO(R66), hydroxy, N(R70)CO($C_1$-$C_6)$-alkyl, or $SO_2CH_3$;

R66, R70 independently of one another H, $(C_1$-$C_8)$-alkyl; the N-oxides thereof and the physiologically tolerated salts thereof.

11. A method of treating obesity comprising administering to a patient in need thereof a therapeutically effective amount of a compound of Formula I as claimed in claim 1 or a pharmaceutically acceptable salt thereof.

12. A method of treating type II diabetes comprising administering to a patient in need thereof a therapeutically effective amount of a compound of Formula I as claimed in claim 1 or a pharmaceutically acceptable salt thereof.

* * * * *